US011343596B2

(12) United States Patent
Chappell, III et al.

(10) Patent No.: US 11,343,596 B2
(45) Date of Patent: May 24, 2022

(54) DIGITALLY REPRESENTING USER ENGAGEMENT WITH DIRECTED CONTENT BASED ON BIOMETRIC SENSOR DATA

(71) Applicant: WARNER BROS. ENTERTAINMENT INC., Burbank, CA (US)

(72) Inventors: Arvel A. Chappell, III, Los Angeles, CA (US); Lewis S. Ostrover, Los Angeles, CA (US)

(73) Assignee: WARNER BROS. ENTERTAINMENT INC., Burbank, CA (US)

( * ) Notice: Subject to any disclaimer, the term of this patent is extended or adjusted under 35 U.S.C. 154(b) by 0 days.

(21) Appl. No.: 16/833,504

(22) Filed: Mar. 27, 2020

(65) Prior Publication Data
US 2020/0296458 A1    Sep. 17, 2020

Related U.S. Application Data

(63) Continuation of application No. PCT/US2018/053614, filed on Sep. 28, 2018.
(Continued)

(51) Int. Cl.
*H04N 21/8545* (2011.01)
*H04N 21/422* (2011.01)
(Continued)

(52) U.S. Cl.
CPC ......... *H04N 21/8545* (2013.01); *A61B 5/163* (2017.08); *A61B 5/165* (2013.01);
(Continued)

(58) Field of Classification Search
None
See application file for complete search history.

(56) References Cited

U.S. PATENT DOCUMENTS 4,305,131 A   12/1981 Best
8,069,125 B2  11/2011 Jung et al.
(Continued)

FOREIGN PATENT DOCUMENTS

WO   WO 2016/172557 A1   10/2016

OTHER PUBLICATIONS

WO, PCT/US2018/053625 ISR and Written Opinion, dated Dec. 27, 2018.

(Continued)

*Primary Examiner* — Alexander Q Huerta
(74) *Attorney, Agent, or Firm* — One LLP

(57) ABSTRACT

A computer-implemented method for obtaining a digital representation of user engagement with audio-video content includes playing digital data comprising audio-video content by an output device that outputs audio-video output based on the digital data and receiving sensor data from at least one sensor positioned to sense an involuntary response of one or more users while engaged with the audio-video output. The method further includes determining a Content Engagement Power (CEP) value, based on the sensor data and recording the digital representation of CEP in a computer memory. An apparatus is configured to perform the method using hardware, firmware, and/or software.

18 Claims, 16 Drawing Sheets

Related U.S. Application Data

(60) Provisional application No. 62/715,766, filed on Aug. 7, 2018, provisional application No. 62/661,556, filed on Apr. 23, 2018, provisional application No. 62/614,811, filed on Jan. 8, 2018, provisional application No. 62/566,257, filed on Sep. 29, 2017.

(51) Int. Cl.
    *H04N 21/45*     (2011.01)
    *H04N 21/8541*     (2011.01)
    *H04N 21/442*     (2011.01)
    *H04N 21/466*     (2011.01)
    *A61B 5/16*     (2006.01)
    *G16H 40/67*     (2018.01)
    *G16H 50/20*     (2018.01)
    *G06F 3/01*     (2006.01)
    *G09B 19/00*     (2006.01)

(52) U.S. Cl.
CPC .............. *G06F 3/011* (2013.01); *G09B 19/00* (2013.01); *G16H 40/67* (2018.01); *G16H 50/20* (2018.01); *H04N 21/42201* (2013.01); *H04N 21/44218* (2013.01); *H04N 21/4532* (2013.01); *H04N 21/4667* (2013.01); *H04N 21/8541* (2013.01)

(56) References Cited

U.S. PATENT DOCUMENTS

| | | | |
|---|---|---|---|
| 9,736,603 B2 | 8/2017 | Osborne et al. | |
| 10,025,972 B2 | 7/2018 | Matas et al. | |
| 10,880,601 B1* | 12/2020 | Donahoe | H04N 21/4302 |
| 2002/0073417 A1 | 6/2002 | Kondo et al. | |
| 2007/0168315 A1 | 7/2007 | Covannon et al. | |
| 2007/0265507 A1* | 11/2007 | de Lemos | A61B 5/16 |
| | | | 600/300 |
| 2008/0161109 A1 | 7/2008 | Chainer et al. | |
| 2010/0070987 A1* | 3/2010 | Amento | H04H 60/33 |
| | | | 725/10 |
| 2010/0211439 A1 | 8/2010 | Marci et al. | |
| 2011/0169603 A1 | 7/2011 | Fithian et al. | |
| 2011/0320536 A1 | 12/2011 | Lobb et al. | |
| 2012/0072939 A1* | 3/2012 | Crenshaw | H04N 21/4415 |
| | | | 725/12 |
| 2012/0324492 A1* | 12/2012 | Treadwell, III | H04H 60/66 |
| | | | 725/10 |
| 2013/0046577 A1* | 2/2013 | Marci | G06Q 10/10 |
| | | | 705/7.29 |
| 2013/0232515 A1* | 9/2013 | Rivera | G06Q 30/02 |
| | | | 725/12 |
| 2013/0247081 A1* | 9/2013 | Vinson | H04N 21/4532 |
| | | | 725/14 |
| 2013/0268954 A1* | 10/2013 | Hulten | H04N 21/442 |
| | | | 725/12 |
| 2013/0280682 A1 | 10/2013 | Levine et al. | |
| 2013/0283162 A1 | 10/2013 | Aronsson et al. | |
| 2014/0130076 A1 | 5/2014 | Moore et al. | |
| 2014/0150002 A1* | 5/2014 | Hough | H04N 21/2668 |
| | | | 725/9 |
| 2014/0221866 A1 | 8/2014 | Quy | |
| 2014/0270683 A1* | 9/2014 | Zhu | H04N 21/42202 |
| | | | 386/224 |
| 2014/0350349 A1 | 11/2014 | Geurts et al. | |
| 2015/0093729 A1 | 4/2015 | Plans et al. | |
| 2015/0127737 A1 | 5/2015 | Thompson et al. | |
| 2015/0142553 A1 | 5/2015 | Kodra et al. | |
| 2015/0181291 A1 | 6/2015 | Wheatley | |
| 2015/0193089 A1 | 7/2015 | Berlin et al. | |
| 2015/0248615 A1* | 9/2015 | Parra | A61B 5/377 |
| | | | 706/12 |
| 2016/0077547 A1 | 3/2016 | Aimone et al. | |
| 2016/0191893 A1 | 6/2016 | Gewickey et al. | |
| 2016/0228744 A1 | 8/2016 | Szacherski | |
| 2017/0055033 A1 | 2/2017 | Christie | |
| 2017/0123824 A1 | 5/2017 | Franck | |
| 2017/0147202 A1 | 5/2017 | Donohue | |
| 2017/0169727 A1 | 6/2017 | Briggs et al. | |
| 2017/0171614 A1* | 6/2017 | el Kaliouby | H04N 21/42203 |
| 2017/0243055 A1 | 8/2017 | Naveh | |
| 2017/0251262 A1* | 8/2017 | Bist | H04N 21/4756 |
| 2018/0205989 A1* | 7/2018 | Srinivasan | G06K 9/00228 |
| 2018/0376187 A1 | 12/2018 | Everett et al. | |
| 2019/0090020 A1* | 3/2019 | Srivastava | G11B 27/28 |
| 2019/0297380 A1 | 9/2019 | Dominguez et al. | |
| 2019/0379938 A1* | 12/2019 | Salo | H04N 21/42201 |
| 2020/0060598 A1* | 2/2020 | Palti-Wasserman | |
| | | | A61B 5/0533 |
| 2020/0134084 A1 | 4/2020 | Rakshit et al. | |
| 2020/0267451 A1 | 8/2020 | Pudhiyaveetil et al. | |
| 2020/0296480 A1 | 9/2020 | Chappell, III et al. | |
| 2020/0297262 A1 | 9/2020 | Chappell, III et al. | |
| 2020/0405212 A1 | 12/2020 | Chappell, III et al. | |
| 2020/0405213 A1 | 12/2020 | Chappell, III et al. | |
| 2021/0056407 A1 | 2/2021 | Buesser et al. | |

OTHER PUBLICATIONS

WO, PCT/US2018/053218 ISR and Written Opinion, dated Jan. 17, 2019.
WO, PCT/US2018/053614 ISR and Written Opinion, dated Jan. 17, 2019.
WO, PCT/US2019/012567 ISR and Written Opinion, dated Apr. 11, 2019.
WO, PCT/US2019/012783 ISR and Written Opinion, dated Apr. 25, 2019.
"#613: Storytelling in VR from a Depth Psychological & Mythological Perspective", 2018, retrieved from https://voicesofvr.com/613-storytelling-in-vr-from-a-depth-psychological-mythological-perspective/, pp. 1-4.
"Ad firms using tools to help them read your mind", 2017, retrieved from https://technology.inquirer.net/70804/ad-firms-using-tools-help-read-mind, pp. 1-7.
Bound, K., "AI: discover how viewer emotions guide the narrative direction of a movie", 2018, retrieved from https://www.linkedin.com/pulse/ai-how-viewer-emotions-guide-narrative-direction-keith, pp. 1-5.
Breland, A., "Facebook patents technology that would estimate users' socioeconomic status", 2018, retrieved from https://thehill.com/policy/technology/372017-facebook-patents-tech-to-estimate-users-socioeconomic-status, pp. 1-2.
Castellanos, S., "Siri Contributor Tackles Software That Detects Emotional States", 2018, retrieved from https://www.wsj.com/articles/siri-contributor-tackles-software-that-detects-emotional-states-1520548561, pp. 1-2.
Chan, S., "Interaxon measures brainwaves to give VR devs more data for game design", 2018, retrieved from https://venturebeat.com/2018/01/13/interaxon-measures-brainwaves-to-give-vr-devs-more-data-for-game-design/, pp. 1-6.
Coldeway, D., "This facial recognition system tracks how you're enjoying a movie", 2017, retrieved from https://techcrunch.com/2017/07/25/this-facial-recognition-system-tracks-how-youre-enjoying-a-movie/, pp. 1-2.
Crooke, J., "Uber applies for patent that would protect drunk passengers", 2018, retrieved from https://techcrunch.com/2018/06/11/uber-applies-for-patent-that-would-detect-drunk-passengers/, pp. 1-3.
Dormehl, L., "Frighteningly accurate 'mind reading' AI reads brain scans to guess what you're thinking", 2017, retrieved from https://www.digitaltrends.com/cool-tech/ai-predicts-what-youre-thinking/, pp. 1-8.
Dormehl, L., "New VR horror game gets scarier if your heart rate isn't fast enough", 218, retrieved from https://www.digitaltrends.com/cool-tech/bring-to-light-heart-rate-vr/, pp. 1-7.
Fadelli, I., "Researchers use machine learning to analyse movie preferences", 2018, retrieved from https://techxplore.com/news/2018-07-machine-analyse-movie.html, pp. 1-3.

(56) References Cited

OTHER PUBLICATIONS

Grant, C., "Many Worlds: The movie that watches its audience", BBQ News, retrieved from https://www.bbc.com/news/technology-21429437, 2013, pp. 1-5.

Harman, A., "Ford Research Gives New Meaning to 'Rush Hour'", 2018, retrieved from https://www.wardsauto.com/industry/ford-research-gives-new-meaning-rush-hour, pp. 1-7.

Hasson, U., et al., "Neurocinematics: The Neuroscience of Film", Projections, 2008, vol. 2, No. 1, pp. 1-26.

Kapur, A., et al., "AlterEgo: A Personalized Wearable Silent Speech Interface", IUI '18: 23rd International Conference on Intelligent User Interfaces, Mar. 2018, Tokyo, Japan, pp. 43-53.

Kaufman, D., "NAB 2018: Machine-Learning Tools to Become Vital for Editing", 2018, retrieved from https://www.etcentric.org/nab-2018-machine-learning-tools-to-beomce-vital-for-editing/), pp. 1-3.

Kaufman, D., "NAB 2018: Potential Impact of AI on Storytelling, Moviemaking", 2018, retrieved from https://www.etcentric.org/nab-2018-potentialimpact-of-ai-on-storytelling-moviemaking/, pp. 1-3.

Lefebvre, R., "MIT's wearable device can 'hear' the words you say in your head", 2018, retrieved from https://www.engadget.com/2018-04-06-mit-wearable-silent-words.html, pp. 1-7.

Marsella, S., et al., "Computational Models of Emotion", Draft Manuscript, pp. 1-30.

Parker, L., "Video Game Creators Seek Ouy Hollywood for Robust Narratives", 2017, retrieved from https://www.nytimes.com/2017/12/20/technology/video-game-creators-hollywood-writers.html#:~:text=When%20Pete%20Samuels%2C%20a%20founder,So%20he%20turned%20to%20Hollywood., pp. 1-4.

Riedl, M. O., et al., "From Linear Story Generation to Branching Story Graphs", IEEE Computer Graphics and Applications, 2006, pp. 23-31.

Siegel, T., "This New Artificial Intelligence Script-Reading Program Could Find Your Next Oscar Role (Exclusive)", 2016, retrieved from https://www.hollywoodreporter.com/news/general-news/new-artificial-intelligence-script-reading-866554/, pp. 1-3.

Solsman, J. E., et al., "Oculus wants to make immersive virtual theater a reality", 2018, retrieved from https://www.cnet.com/tech/mobile/oculus-wants-to-make-immersive-virtual-theater-a-reality/, pp. 1-4.

Simonite, T., "This Call May Be Monitored for Tone and Emotion", 2018, retrieved from https://www.wired.com/story/this-call-may-be-monitored-for-tone-and-emotion/, pp. 1-8.

Trew, J., "Dolby knows what you're feeling at the movies", 2018, retrieved from https://www.engadget.com/2018-01-12-dolby-knows-what-youre-watching-based-on-your-b.html, pp. 1-5.

"Turning Design Mockups Into Code With Deep Learning", 2018, retrieved from https://blog.floydhub.com/turning-design-mockups-into-code-with-deep-learning/, pp. 1-41.

Waltz, E., "A New Wearable Brain Scanner", 2018, retrieved from https://spectrum.ieee.org/the-human-os/biomedical/imaging/a-new-wearable-brain-scanner, pp. 1-4.

Wang, J., et al., "Predicting the Brain Activation Pattern Associated With the Propositional Content of a Sentence: Modeling Neural Representations of Events and States", Human Brain Mapping, 2017, vol. 38, No. 10, pp. 4865-4881.

Webb, A., "Apple Is Developing an EKG Heart Monitor for Its Smartwatch", 2017, retrieved from https://www.bloomberg.com/news/articles/2017-12-21/apple-is-said-to-develop-ekg-heart-monitor-for-future-watch, pp. 1-2.

"Aside", 2016, retrieved from https://web.archive.org/web/20161117103448/htpps://en.wikipedia.org/wiki/Aside, 2 pages.

Turk, V., "Shakespeare, Remixed by Biosensors", 2014, retrieved from https://www.vice.com/en/article/bmjmd8/shakespeare-remixed-by-biosensors, 7 pages.

EP, 19736258.5 Supplementary Search Report, dated Oct. 26, 2021.
EP, 19735809.6 Partial Supplementary Search Report, dated Nov. 4, 2021.

Gilroy, S. W., et al., "Exploring Passive User Interaction for Adaptive Narratives", Proceedings of the 2012 ACM international conference on Intelligent User Interfaces, 2012, Session: Designing Narratives & Theater, Lisbon, Portugal, pp. 119-128.

Katti, H., et al., "Affective video summarization and story board generation using Pupillary dilation and Eye gaze", 2011 IEEE International Symposium on Multimedia, 2011, Dana Point, CA, pp. 319-326.

Sourina, O., et al., "EEG-Based Personalized Digital Experience", International Conference on Universal Access in Human-Computer Interaction, 2011, pp. 591-599.

EP, 18861951.4 Extended Search Report, dated Aug. 9, 2021.

* cited by examiner

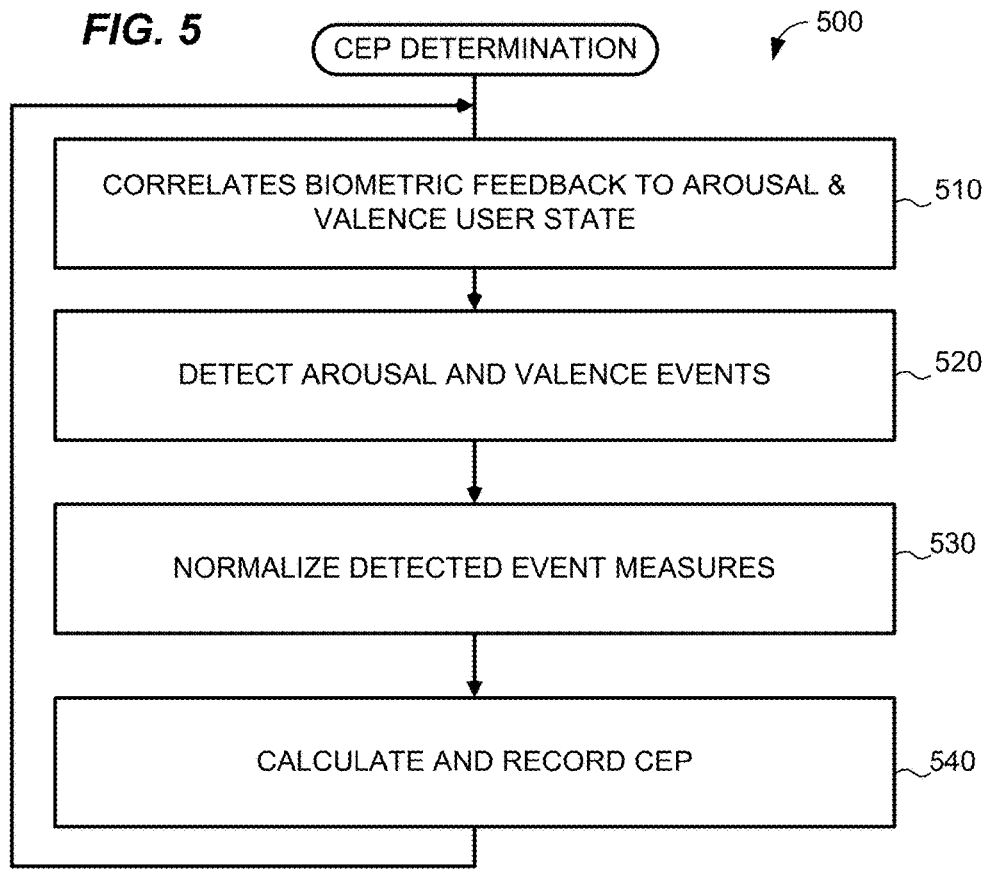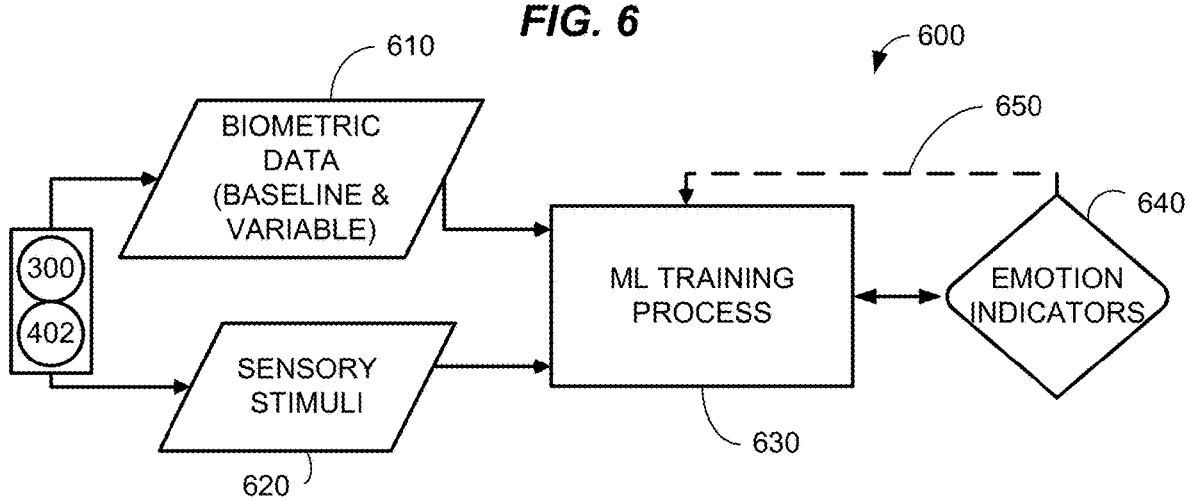

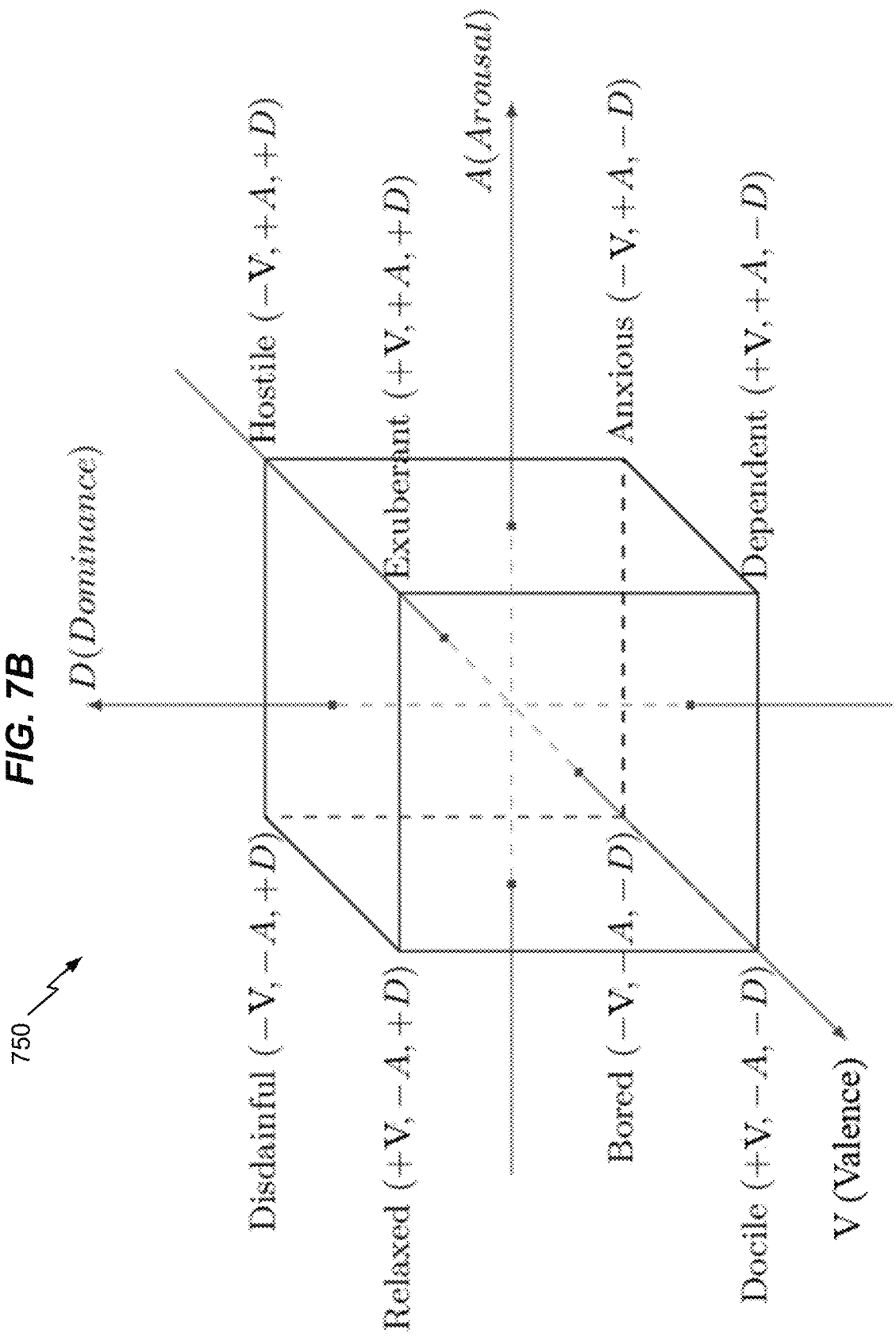

| Brow Furrow | Brow Raise | Engagement | Lip Corner Depressor | Smile | Valence | Attention | Interocular | Pitch | Yaw | Roll | InnerBrowRaise | EyeClosure | NoseWrinkle |
|---|---|---|---|---|---|---|---|---|---|---|---|---|---|
| 0.03507038 | 0.1258643 | 0.08256674 | 0.00019858 | 0.053036 | 0 | 97.33481 | | 0 | 0 | 0 | 0.095351 | 0.000978749 | 0.02849308 |
| 0.01532619 | 0.1573996 | 0.09077279 | 0.00018302 | 0.082795 | 0 | 96.8397 | | 0 | 0 | 0 | 0.06684729 | 0.01816105 | 0.03999165 |
| 0.008455852 | 0.1309778 | 0.09143862 | 0.000180222 | 0.070813 | 0 | 95.20685 | | 0 | 0 | 0 | 0.052416 | 0.02312578 | 0.03903106 |
| 0.01087985 | 0.1571735 | 0.08767586 | 0.000207608 | 0.060567 | 0 | 97.15795 | | 0 | 0 | 0 | 0.06066076 | 0.203134 | 0.03522376 |
| 0.01447419 | 0.1771761 | 0.08739696 | 0.000267503 | 0.062191 | 0 | 95.97399 | | 0 | 0 | 0 | 0.06128005 | 0.08917413 | 0.03747093 |
| 0.01399511 | 0.1575872 | 0.08761833 | 0.000247085 | 0.059986 | 0 | 96.24033 | | 0 | 0 | 0 | 0.05964601 | 0.09347043 | 0.04183157 |
| 0.01514081 | 0.1548829 | 0.08705284 | 0.000257574 | 0.056657 | 0 | 95.28419 | | 0 | 0 | 0 | 0.0651888 | 0.06793306 | 0.04717053 |
| 0.01126526 | 0.1572145 | 0.08686806 | 0.000243876 | 0.05299 | 0 | 95.59425 | | 0 | 0 | 0 | 0.06135362 | 0.03098076 | 0.0397791 |
| 0.01166921 | 0.1558826 | 0.08721946 | 0.000247955 | 0.056862 | 0 | 95.57716 | | 0 | 0 | 0 | 0.06304643 | 0.093227 | 0.04003891 |
| 0.00955689 | 0.1576587 | 0.08781804 | 0.000259257 | 0.062282 | 0 | 95.55119 | | 0 | 0 | 0 | 0.05865594 | 0.08620712 | 0.03878407 |
| 0.009042143 | 0.1521303 | 0.08734642 | 0.000262112 | 0.061754 | 0 | 95.72122 | | 0 | 0 | 0 | 0.06168778 | 0.05781268 | 0.03517428 |

| UpperLipRaise | ChinRaise | Smirk | LipPucker | Anger | Sadness | Disgust | Joy | Surprise | Fear | Contempt | Cheek Raise | Dimpler | Eye Widen | Lid Tighten | Lip Stretch |
|---|---|---|---|---|---|---|---|---|---|---|---|---|---|---|---|
| 0.4923475 | 0.015718 | 0.003574 | 0.010368 | 0.001995 | 0.023677 | 0.437966 | 0.001850 | 0.196973 | 0.004492 | 0.192109 | 0.000135 | 0.02194 | 1.62E-06 | 0.123071 | 0.020959 |
| 1.149534 | 0.021841 | 0.002022 | 0.052891 | 0.002072 | 0.022535 | 0.460138 | 0.001904 | 0.203964 | 0.004471 | 0.191579 | 0.000131 | 0.018255 | 8.06E-06 | 0.10226 | 0.018549 |
| 1.517288 | 0.023302 | 0.001998 | 0.022825 | 0.002085 | 0.02244 | 0.464810 | 0.001907 | 0.204505 | 0.004471 | 0.191726 | 0.000166 | 0.014169 | 1.35E-05 | 0.090357 | 0.013812 |
| 1.202922 | 0.024733 | 0.001738 | 0.020918 | 0.002042 | 0.022923 | 0.457567 | 0.001881 | 0.201683 | 0.00447 | 0.191876 | 0.000268 | 0.017576 | 1.51E-05 | 0.101771 | 0.015869 |
| 1.573044 | 0.024618 | 0.001844 | 0.02680 | 0.002035 | 0.022966 | 0.464009 | 0.001877 | 0.201293 | 0.004475 | 0.191868 | 0.000387 | 0.014483 | 1.58E-05 | 0.097801 | 0.012134 |
| 1.861519 | 0.027034 | 0.002082 | 0.026174 | 0.002041 | 0.022935 | 0.470225 | 0.001880 | 0.201391 | 0.004478 | 0.191903 | 0.00034 | 0.013166 | 1.19E-05 | 0.09573 | 0.010647 |
| 2.000099 | 0.02848 | 0.002335 | 0.027024 | 0.002037 | 0.023020 | 0.472471 | 0.001876 | 0.200919 | 0.00448 | 0.19196 | 0.00041 | 0.014782 | 1.19E-05 | 0.107207 | 0.011561 |
| 2.446125 | 0.027306 | 0.002468 | 0.022226 | 0.002033 | 0.023035 | 0.480584 | 0.001874 | 0.200870 | 0.004478 | 0.192001 | 0.000331 | 0.016505 | 1.15E-05 | 0.095612 | 0.012491 |
| 2.341053 | 0.02835 | 0.002663 | 0.025695 | 0.002226 | 0.023088 | 0.478927 | 0.001877 | 0.201135 | 0.004478 | 0.19195 | 0.00034 | 0.016393 | 1.21E-05 | 0.099784 | 0.012311 |
| 2.462923 | 0.033536 | 0.003002 | 0.023219 | 0.002042 | 0.022892 | 0.481866 | 0.001882 | 0.201538 | 0.004479 | 0.191873 | 0.000442 | 0.013488 | 1.01E-05 | 0.094638 | 0.011198 |
| 2.367024 | 0.033225 | 0.003252 | 0.022751 | 0.002038 | 0.022953 | 0.479208 | 0.00188 | 0.201126 | 0.004481 | 0.191884 | 0.000432 | 0.014938 | 1.11E-05 | 0.096711 | 0.01175 |

Abbreviations: A = Arousal, V = Valance, * = Preferred, ** = Most Preferred

Table of Biometric Inputs for Measurement of Content Engagement Power ⟵1100

| | Measurement Type | Measure of: | A-Weight | V-Weight |
|---|---|---|---|---|
| 1 | ** EEG (Electroencephalography) | A, V | H | H |
| 2 | ** GSR (Galvanic Skin Response) | A | - | H |
| 3 | * FAU (Facial Action Units – by image analysis) | A, V | L | H |
| 4 | * Pulse detection (audio or video analysis) | A | M | - |
| 5 | * Pupil dilation (image analysis) | A | H | - |
| 6 | * fNIR (Functional Near Infrared) | A, V, skin temperature | H | H |
| 7 | fEMG (facial Electromyography) | A, V | M | M |
| 8 | Subvocalization or vocalization detection | A, V | M | M |
| 9 | EKG (Electrocardiography) | A | M | - |
| 10 | BMI (Brain Machine Interface) | A, V | H | H |
| 11 | fMRI (functional Magnetic Resonance Imaging) | A, V | H | H |
| 12 | Chemical detection (e.g., spectral analysis or chemical sensor) | V | - | L |
| 13 | PPG (Photoplethysmography) | A | H | - |
| 14 | PET (Positron Emission Tomography) | A, V | L | H |
| 15 | ** Gaze Direction | Interest | - | - |

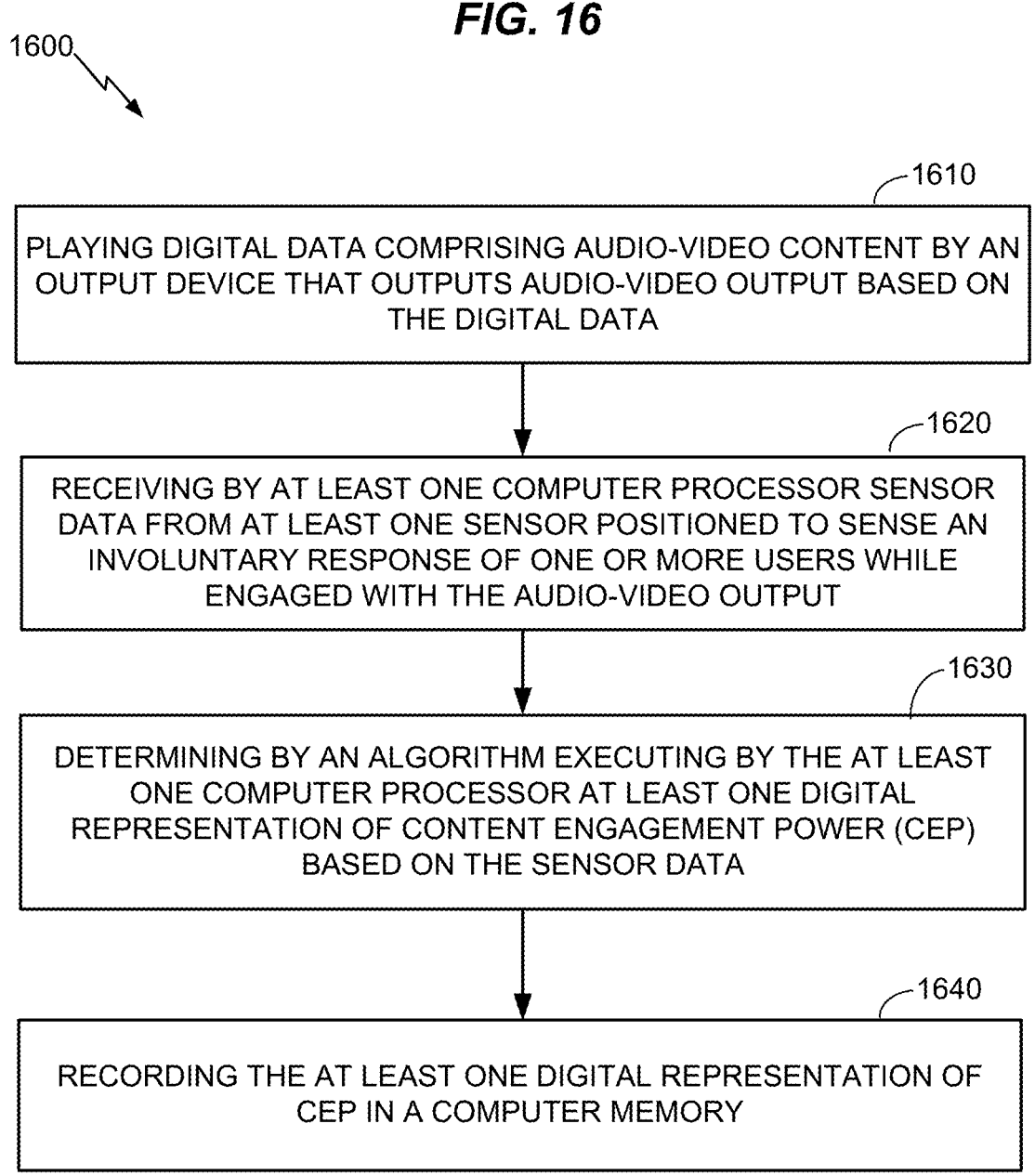

1710 — DETERMINING THE AT LEAST ONE DIGITAL REPRESENTATION OF CEP FURTHER COMPRISES DETERMINING AROUSAL VALUES BASED ON THE SENSOR DATA AND COMPARING A STIMULATION AVERAGE AROUSAL BASED ON THE SENSOR DATA WITH AN EXPECTATION AVERAGE AROUSAL

1720 — DETERMINING THE EXPECTATION AVERAGE AROUSAL BASED ON FURTHER SENSOR DATA MEASURING A LIKE INVOLUNTARY RESPONSE OF THE ONE OR MORE USERS WHILE ENGAGED WITH KNOWN AUDIO-VIDEO STIMULI

1730 — PLAYING THE KNOWN AUDIO-VIDEO STIMULI COMPRISING A KNOWN NON-AROUSING STIMULUS AND A KNOWN AROUSING STIMULUS

1740 — DETECTING ONE OR MORE STIMULUS EVENTS, AND CALCULATING ONE OF MULTIPLE EVENT POWERS FOR EACH OF THE ONE OR MORE USERS AND FOR EACH OF THE STIMULUS EVENTS, AND AGGREGATING THE EVENT POWERS

1750 — DETECTING ONE OR MORE STIMULUS EVENTS BASED ON THE FURTHER SENSOR DATA EXCEEDING A THRESHOLD VALUE FOR A TIME PERIOD, AND CALCULATING ONE OF MULTIPLE EXPECTATION POWERS FOR THE KNOWN AUDIO-VIDEO STIMULI FOR THE ONE OR MORE USERS AND FOR EACH OF THE STIMULUS EVENTS

1760 — DETERMINING THE AT LEAST ONE DIGITAL REPRESENTATION OF CEP COMPRISES CALCULATING A RATIO OF THE SUM OF THE EVENT POWERS TO AN AGGREGATE OF THE EXPECTATION POWERS

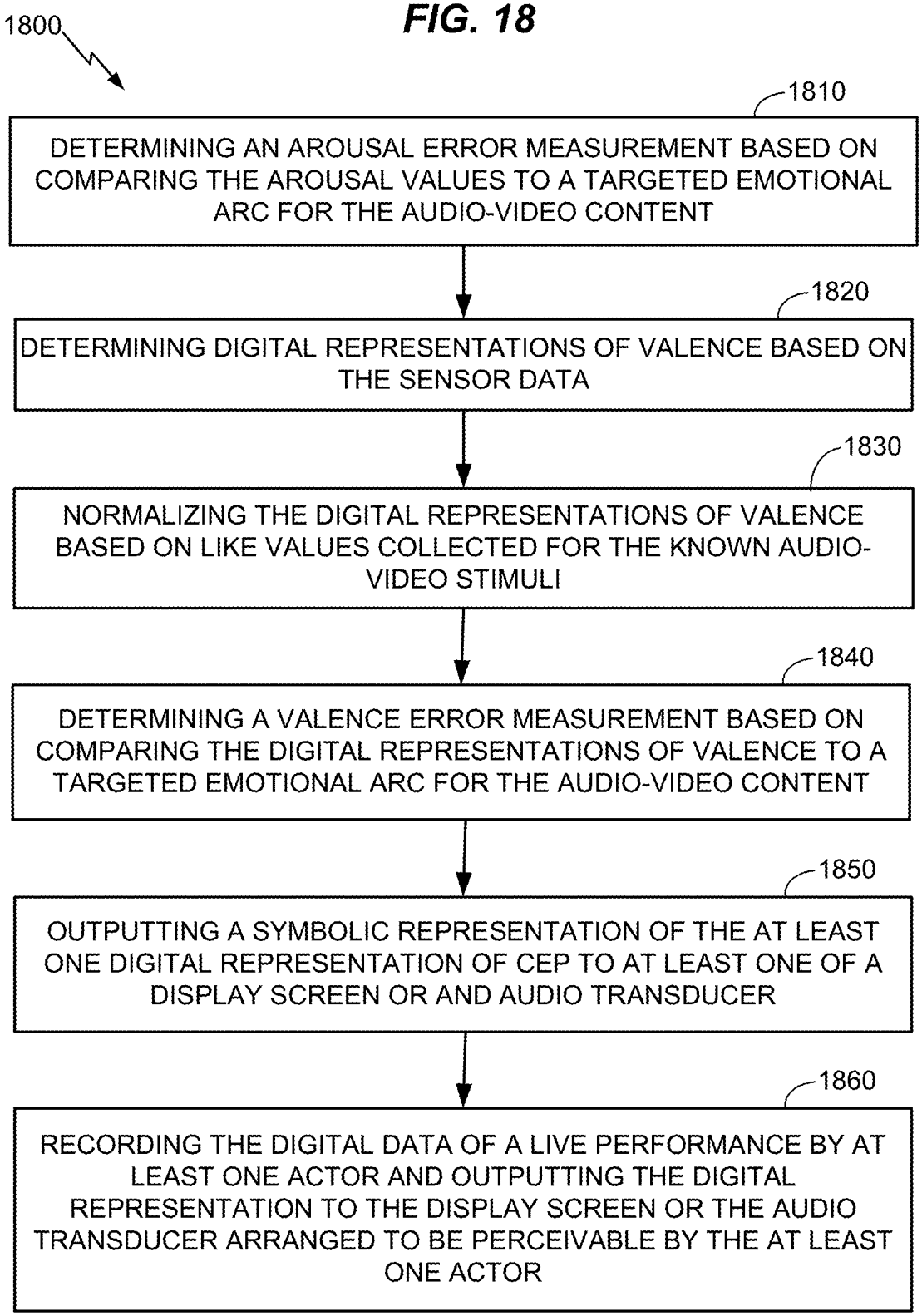

DIGITALLY REPRESENTING USER ENGAGEMENT WITH DIRECTED CONTENT BASED ON BIOMETRIC SENSOR DATA

CROSS-REFERENCE TO RELATED APPLICATION

The present application is a continuation of International (PCT) application No. PCT/US2018/053614 filed Sep. 28, 2018, which claims priority to U.S. provisional patent applications Ser. No. 62/715,766 filed Aug. 7, 2018, Ser. No. 62/661,556 filed Apr. 23, 2018, Ser. No. 62/614,811 filed Jan. 8, 2018, and Ser. No. 62/566,257 filed Sep. 29, 2017, the disclosures of all of which are incorporated herein in their entireties by reference.

FIELD

The present disclosure relates to methods and apparatus for rating user engagement with digital directed content, based on sensor data indicating a user's emotional state.

BACKGROUND

While new entertainment mediums and ever more spectacular effects entertain viewers as never before, the foundation for directed content remains the story and the actor. Successful movies combine compelling stories with convincing actors and visually and acoustically appealing arrangements usually aimed at the broadest possible audience for a film's genre. Production decisions are based on the director's artistic and business sensibilities often formed years or months prior to initial release. Large production budgets are spent on a fixed product that most viewers will see only once. The end product is the same for everybody, all the time. Directors cannot possibly deliver a product that everyone will empathize with, so they create for a common denominator or market niche.

One technique for narrative content is branching. Branching narratives in computer-generated audio-video entertainment date back to the 1980's or earlier. Sophisticated video games of the present day blur the boundary between narrative and interactive entertainment, blending branching and interactive techniques. Immersive entertainment technologies such as virtual and augmented reality bring further opportunities to enthrall viewers. Data mining by machine learning enables discovery of new correspondences between low-level data and various targets, including consumer preferences and propensities. Proliferation of mobile phones and Internet of Things (IoT) devices drive an explosion of network-connected sensors. It is now possible to gather more real-time and batch data about consumers of content than ever before.

Apart from branching, content producers use many techniques to gauge the appeal of planned content before committing to production. Once a feature has been produced, surveys, focus groups, and test marketing may be done to fine-tune the content narrative and plan marketing strategies. Accurate and fine-grained audience response data is difficult and time-consuming to gather by traditional methods.

It would be desirable, therefore, to develop new methods and other new technologies for rating user engagement with directed content, that overcome these and other limitations of the prior art and help producers deliver more compelling entertainment experiences for the audiences of tomorrow.

SUMMARY

This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures.

In an aspect of the disclosure, a computer-implemented method for digitally representing user engagement with audio-video content in a computer memory includes playing digital data comprising audio-video content by an output device that outputs audio-video output based on the digital data. "User" means an audience member, a person experiencing directed content as a consumer for entertainment purposes. The method further includes receiving by at least one computer processor sensor data from at least one sensor positioned to sense an involuntary response of one or more users while engaged with the audio-video output. For example, the sensor data may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic imaging (fMRI) data, body chemical sensing data and functional near-infrared data (fNIR) received from corresponding sensors. The method may further include determining by an algorithm executing by the at least one computer processor at least one digital representation of Content Engagement Power (CEP) based on the sensor data and recording the at least one digital representation of CEP in a computer memory. Suitable algorithms are described in the detailed description that follows.

CEP is an objective, algorithmic and digital electronic measure of a user's biometric state that correlates to engagement of the user with a stimulus, namely directed content. We use two orthogonal measures for CEP, arousal and valence. As used herein, "arousal" is used in accordance with its meaning in psychology to mean a state or condition of being physiologically alert, awake and attentive. High arousal indicates interest and attention, low arousal indicates boredom and disinterest. "Valence" is also used here in its psychological sense of attractiveness or goodness. Positive valence indicates attraction, and negative valence indicates aversion.

The at least one digital representation of CEP may include a sequence of digital representations of CEP wherein each member of the sequence is calculated based on a discrete period in the audio-video content. The method may include outputting a symbolic representation of the at least one digital representation of CEP to at least one of a display screen or and audio transducer. In some embodiments, the method may include recording the digital data during a live performance by at least one actor and arranging the display screen or the audio transducer to be perceivable by the at least one actor still during the live performance.

In an aspect, determining the at least one digital representation of CEP further comprises determining arousal values based on the sensor data and comparing a stimulation average arousal based on the sensor data with an expectation average arousal. The method may include determining the expectation average arousal based on further sensor data measuring a like involuntary response of the one or more users while engaged with known audio-video stimuli. The expectation average arousal is a digital representation of each user's arousal response to known stimuli, for use in normalizing differences between individual users. The method may further include playing the known audio-video stimuli comprising a known non-arousing stimulus and a known arousing stimulus, optionally while noting materially different circumstances of individual users, e.g. the user's initial state of arousal, mood, fatigue, rest, health, medication or intoxication.

In another aspect, determining the at least one digital representation of CEP may include detecting one or more stimulus events based on the sensor data exceeding a threshold value for a time period. In addition, the method may include calculating one of multiple event powers for each of the one or more users and for each of the stimulus events and aggregating the event powers. The method may include assigning weights to each of the event powers based on one or more source identities for the sensor data. Determining the expectation average arousal may further include detecting one or more stimulus events based on the further sensor data exceeding a threshold value for a time period and calculating one of multiple expectation powers for the known audio-video stimuli for the one or more users and for each of the stimulus events. Determining the at least one digital representation of CEP may include calculating a ratio of the sum of the event powers to an aggregate of the expectation powers.

In another aspect, the method may include determining an arousal error measurement based on comparing the arousal values to a targeted emotional arc for the audio-video content. The targeted emotional arc may include a set of targeted arousal values each uniquely associated with a different interval of a continuous time sequence, and the method may include determining digital representations of valence based on the sensor data.

As part of determining the digital representation of the CEP, or for other uses, the method may include determining a digital representation of user valence based on the sensor data. Sensor data suitable for valence determination may include, for example, any one or more of electroencephalographic (EEG) data, facial electromyography (fEMG) data, video facial action unit (FAU) data, brain machine interface (BMI) data, functional magnetic imaging (fMRI) data, body chemical sensing data, and functional near-infrared data (fNIR). The method may include normalizing the digital representations of valence based on like values collected for the known audio-video stimuli. In an aspect, the method may include determining a valence error measurement based on comparing the digital representations of valence to a targeted emotional arc for the audio-video content. The targeted emotional arc may be or may include a set of targeted digital representations of valence and/or arousal each uniquely associated with a different interval of a continuous time sequence or frame sequence for digital audio-video content.

The foregoing method may be implemented in any suitable programmable computing apparatus, by provided program instructions in a non-transitory computer-readable medium that, when executed by a computer processor, cause the apparatus to perform the described operations. The processor may be local to the apparatus and user, located remotely, or may include a combination of local and remote processors. An apparatus may include a computer or set of connected computers that is used in production of directed content for content output devices. A content output device may include, for example, a personal computer, mobile phone, notepad computer, a television or computer monitor, a projector, a virtual reality device, or augmented reality device. Other elements of the apparatus may include, for example, an audio output device and a user input device, which participate in the execution of the method. An apparatus may include a virtual or augmented reality device, such as a headset or other display that reacts to movements of a user's head and other body parts. The apparatus may include biometric sensors that provide data used by a controller to determine a digital representation of CEP.

To the accomplishment of the foregoing and related ends, one or more examples comprise the features hereinafter fully described and particularly pointed out in the claims. The following description and the annexed drawings set forth in detail certain illustrative aspects and are indicative of but a few of the various ways in which the principles of the examples may be employed. Other advantages and novel features will become apparent from the following detailed description when considered in conjunction with the drawings and the disclosed examples, which encompass all such aspects and their equivalents.

BRIEF DESCRIPTION OF THE DRAWINGS

The features, nature, and advantages of the present disclosure will become more apparent from the detailed description set forth below when taken in conjunction with the drawings in which like reference characters identify like elements correspondingly throughout the specification and drawings.

FIG. 5 is a flow chart illustrating high-level operation of a method determining a digital representation of CEP based on biometric sensor data collected during performance of directed content.

FIG. 6 is a block diagram illustrating high-level aspects of a system for digitally representing user engagement with audio-video content in a computer memory based on biometric sensor data.

FIG. 7B is a diagram indicating an arrangement of emotional states relative to axes of a three-dimensional emotional space.

FIG. 8 is a data table illustrating an example of output from an application for measuring Facial Action Units (FAU).

FIG. 11 is a table illustrating biometric input options for measurement of content engagement power.

FIG. 16 is a flow chart illustrating aspects of a method for digitally representing user engagement with audio-video content in a computer memory based on biometric sensor data.

FIGS. 17-18 are flow charts illustrating further optional aspects or operations of the method diagrammed in FIG. 16.

DETAILED DESCRIPTION

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form to facilitate describing these aspects.

Figure 1:
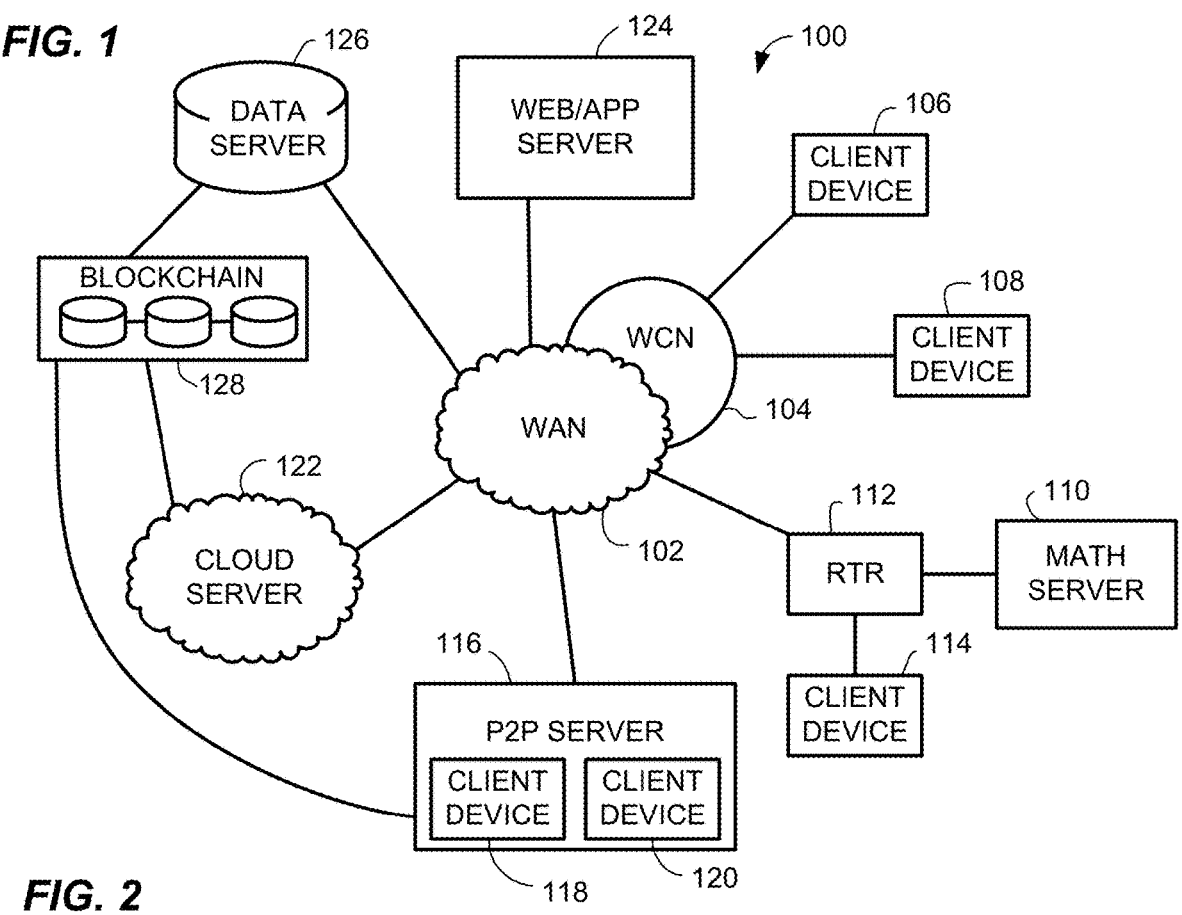
FIG. 1 is a schematic block diagram illustrating aspects of a system and apparatus for digitally representing user engagement with audio-video content in a computer memory based on biometric sensor data, coupled to one or more distribution systems.

Referring to FIG. 1, methods for digitally representing user engagement with audio-video content in a computer memory based on biometric sensor data may be implemented in a client-server environment 100. Other architectures may also be suitable. In a network architecture, sensor data can be collected and processed locally, and transmitted to a server that calculates a digital representation of user engagement with audio-video content in a computer memory based on biometric sensor data. As used herein, "directed content" refers to digital audio-video content that is directed at least in part according to a scheme designed to entertain or inform while evoking emotions in viewers according to a plan for modulating narrative tension sometime referred to herein as an "emotional arc." Directed content is not limited to content presented in a cinema or to cinema-length features, and may include any audio-video content, including content for mobile phones and other small screens, VR and AR content, and interactive games that include narrative elements even if also including non-narrative elements. The narrative tension planned by an emotional arc may cause the user to experience feelings of opposite polarity, e.g., fear and confidence or aversion and attraction at different times or in response to certain dramatic events, characters, objects, images, sounds, music, or other stimuli generated from the digital audio-video content. The intensity of these feelings often relates to the interest and pleasure the user gains from the experience and can also be planned by the emotional arc as tension builds, climaxes, and is relieved. Users of cinematic content naturally react during experience of the emotional arc by involuntarily entering neurological or neurophysiological states in tension (e.g., positive or negative emotions sometimes called valence, and intensity, amplitude or strength of the response, sometimes called arousal).

The directed content may also be configured to support interactive features resembling video game features or may be devoid of interactive features. Directed content may branch in response to data indicative of user emotions or may be non-branching. In addition to content produced using traditional scripts, directed content may include programs that are directed using tools other than traditional scripts, for example, game shows, variety shows, documentaries and reality shows.

Users of directed content react by natural expression of their emotions during their experience of visible, audible, olfactory or tactile sensations generated by an output device that receives directed content signal. If the directed content is configured to support it, users (more exactly, "player actors") may also actively interact with characters or other objects appearing in the directed content. As used herein, a "player actor" is a user of a client device or interface equipped with or coupled to biometric sensors, who uses the client device or interface to interact with directed content by involuntarily entering a neurological or neurophysiological state (e.g., emoting) that is detected by the biometric sensors, whether or not also using a controller to provide direct input, such that the directed content is altered in response to the sensed biometric responses without requiring an intentional action by the player actor. A data processing server such as "math" server 110 may receive the sensor data from the biometric sensors positioned to detect the neurological, neurophysiological or physiological responses of audience members during consumption of directed content. The server 100 may process the sensor data to obtain a digital representation indicative of the audience's neurological, neurophysiological or physiological responses (for convenience, "emotional responses") to the directed content, as a function of time or video frame, indicated along one or more measurement axes (e.g., arousal and valence). In alternative embodiments, content-adaptive artificial intelligence (AI) may adapt the directed content to increase or maintain engagement by the player actor for character viewpoints in the narrative, based on real time emotional feedback.

A suitable client-server environment 100 may include various computer servers and client entities in communication via one or more networks, for example a Wide Area Network (WAN) 102 (e.g., the Internet) and/or a wireless communication network (WCN) 104, for example a cellular telephone network. Computer servers may be implemented in various architectures. For example, the environment 100 may include one or more Web/application servers 124 containing documents and application code compatible with World Wide Web protocols, including but not limited to HTML, XML, PHP and JavaScript documents or executable scripts, for example. The Web/application servers 124 may serve applications for outputting directed content and for collecting biometric sensor data from users experiencing the directed content. In an alternative, and data collection applications may be served from a math server 110, cloud server 122, blockchain entity 128, or content data server 126.

The environment 100 may include one or more data servers 126 for holding data, for example video, audio-video, audio, and graphical content components of directed content for consumption using a client device, software for execution on or in conjunction with client devices, for example sensor control and emotion detection applications, and data collected from users or client devices. Data collected from client devices or users may include, for example, sensor data and application data. Sensor data may be collected by a background (not user-facing) application operating on the client device, and transmitted to a data sink, for example, a cloud-based data server 122 or discrete data server 126. Application data means application state data, including but not limited to records of user interactions with an application or other application inputs, outputs or internal states. Applications may include software for outputting directed content, collecting biometric sensor data and supporting functions. Applications and data may be served from other types of servers, for example, any server accessing a distributed blockchain data structure 128, or a peer-to-peer (P2P) server 116 such as may be provided by a set of client devices 118, 120 operating contemporaneously as microservers or clients.

As used herein, "users" are always consumers of directed content from which a system node collects emotional response data for use in determining a digital representation of engagement with directed content. When actively participating in content via an avatar or other agency, users may also be referred to herein as player actors. Viewers are not always users. For example, a bystander may be a passive viewer from which the system collects no emotional response data. As used herein, a "node" includes a client or server participating in a computer network.

The network environment 100 may include various client devices, for example a mobile smart phone client 106 and notepad client 108 connecting to servers via the WCN 104 and WAN 102 or a mixed reality (e.g., virtual reality or augmented reality) client device 114 connecting to servers via a router 112 and the WAN 102. In general, client devices may be, or may include, computers used by users to access directed content provided via a server or from local storage. In an aspect, the data processing server 110 may determine digital representations of biometric data for use in real-time or offline applications. Controlling branching or the activity of objects in narrative content is an example of a real-time application. Offline applications may include, for example, "green lighting" production proposals, automated screening of production proposals prior to green lighting, automated or semi-automated packaging of promotional content such as trailers or video ads, customized editing of content for users or user cohorts (both automated and semi-automated).

Figure 2:
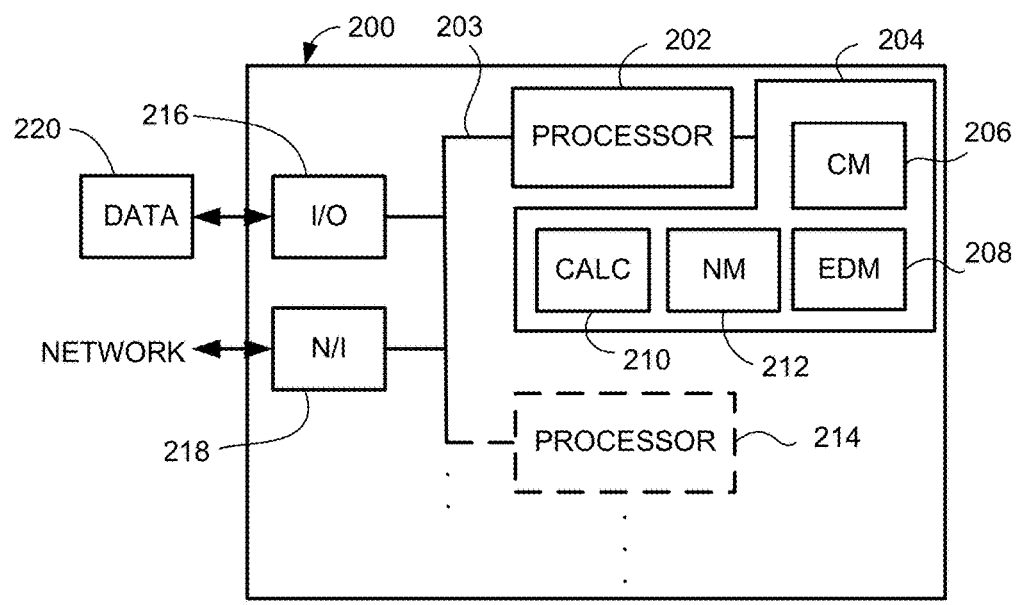
FIG. 2 is a schematic block diagram illustrating aspects of a server for digitally representing user engagement with audio-video content in a computer memory based on biometric sensor data.

FIG. 2 shows a data processing server 200 for digitally representing user engagement with audio-video content in a computer memory based on biometric sensor data, which may operate in the environment 100, in similar networks, or as an independent server. The server 200 may include one or more hardware processors 202, 214 (two of one or more shown). Hardware includes firmware. Each of the one or more processors 202, 214 may be coupled to an input/output port 216 (for example, a Universal Serial Bus port or other serial or parallel port) to a source 220 for sensor data indicative of users' emotional states and viewing history. Viewing history may include a log-level record of variances from a baseline script for a content package or equivalent record of control decisions made in response to player actor emotional states and other input. Viewing history may also include content viewed on TV, Netflix and other sources. Any source that contains a derived emotional arc may be useful for input to an algorithm for digitally representing user engagement with audio-video content in a computer memory based on biometric sensor data. The server 200 may track player actor actions and emotional responses across multiple content titles for individuals or cohorts. Some types of servers, e.g., cloud servers, server farms, or P2P servers, may include multiple instances of discrete servers 200 that cooperate to perform functions of a single server.

The server 200 may include a network interface 218 for sending and receiving applications and data, including but not limited to sensor and application data used for digitally representing user engagement with audio-video content in a computer memory based on biometric sensor data. The content may be served from the server 200 to a client device or stored locally by the client device. If stored local to the client device, the client and server 200 may cooperate to handle collection of sensor data and transmission to the server 200 for processing.

Each processor 202, 214 of the server 200 may be operatively coupled to at least one memory 204 holding functional modules 206, 208, 210, 212 of an application or applications for performing a method as described herein. The modules may include, for example, a correlation module 206 that correlates biometric feedback to one or more metrics such as arousal or valence. The correlation module 206 may include instructions that when executed by the processor 202 and/or 214 cause the server to correlate biometric sensor data to one or more physiological or emotional states of the user, using machine learning (ML) or other processes. An event detection module 208 may include functions for detecting events based on an emotional measure exceeding a data threshold. The modules may further include, for example, a normalization module 210. The normalization module 210 may include instructions that when executed by the processor 202 and/or 214 cause the server to normalize measure valence, arousal, or other values using a baseline input. The modules may further include a calculation function 212 that when executed by the processor causes the server to calculate a Content Engagement Power (CEP) based on the sensor data and other output from upstream modules. Details of determining a CEP are disclosed later herein. The memory 204 may contain additional instructions, for example an operating system, and supporting modules.

Figure 3:
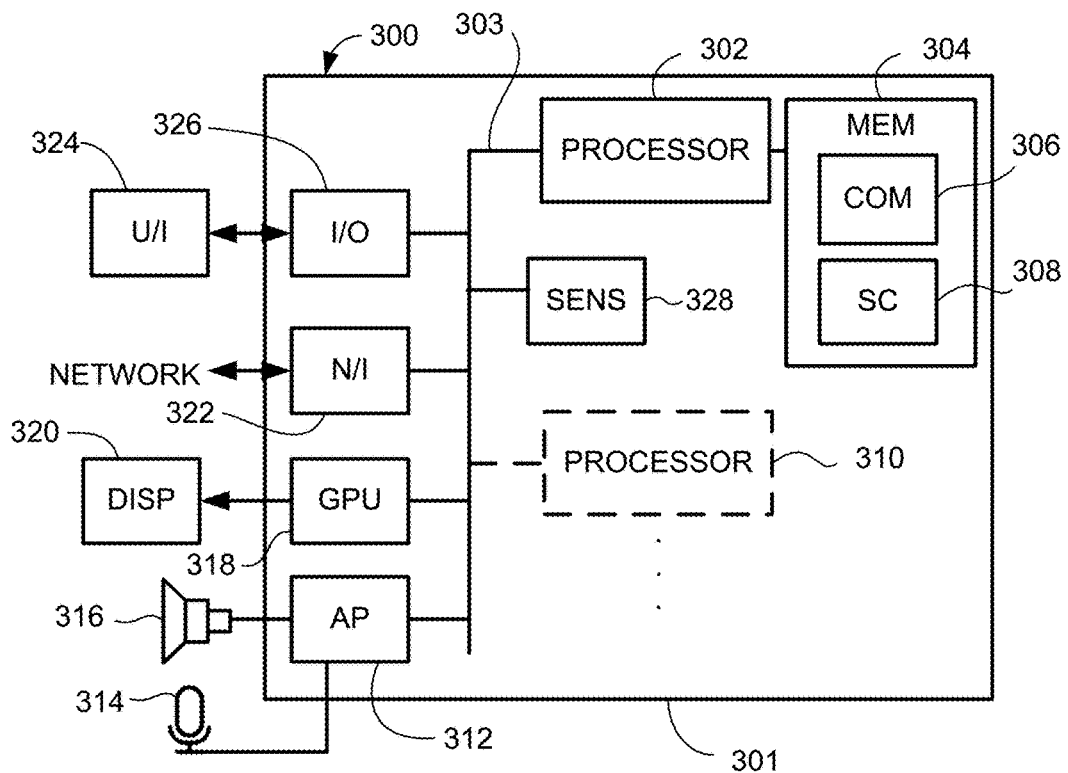
FIG. 3 is a schematic block diagram illustrating aspects of a client device for digitally representing user engagement with audio-video content in a computer memory based on biometric sensor data.

Referring to FIG. 3, a content consumption device 300 generates biometric sensor data indicative of a user's physiological or emotional response to output generated from a directed content signal. The apparatus 300 may include, for example, a processor 302, for example a central processing unit based on 80×86 architecture as designed by Intel™ or AMD™, a system-on-a-chip as designed by ARM™, or any other suitable microprocessor. The processor 302 may be communicatively coupled to auxiliary devices or modules of the 3D environment apparatus 300, using a bus or other coupling. Optionally, the processor 302 and its coupled auxiliary devices or modules may be housed within or coupled to a housing 301, for example, a housing having a form factor of a television, set-top box, smartphone, wearable googles, glasses, or visor, or other form factor.

A user interface device 324 may be coupled to the processor 302 for providing user control input to a media player and data collection process. The process may include outputting video and audio for a conventional flat screen or projection display device. In some embodiments, the directed content control process may be, or may include, audio-video output for an immersive mixed reality content display process operated by a mixed reality immersive display engine executing on the processor 302.

User control input may include, for example, selections from a graphical user interface or other input (e.g., textual or directional commands) generated via a touch screen, keyboard, pointing device (e.g., game controller), microphone, motion sensor, camera, or some combination of these or other input devices represented by block 324. Such user interface device 324 may be coupled to the processor 302 via an input/output port 326, for example, a Universal Serial Bus (USB) or equivalent port. Control input may also be provided via a sensor 328 coupled to the processor 302. A sensor 328 may be or may include, for example, a motion sensor (e.g., an accelerometer), a position sensor, a camera or camera array (e.g., stereoscopic array), a biometric temperature or pulse sensor, a touch (pressure) sensor, an altimeter, a location sensor (for example, a Global Positioning System (GPS) receiver and controller), a proximity sensor, a motion sensor, a smoke or vapor detector, a gyroscopic position sensor, a radio receiver, a multi-camera tracking sensor/controller, an eye-tracking sensor, a microphone or a microphone array, an electroencephalographic (EEG) sensor, a galvanic skin response (GSR) sensor, a facial electromyography (fEMG) sensor, an electrocardiogram (EKG) sensor, a video facial action unit (FAU) sensor, a brain machine interface (BMI) sensor, a video pulse detection (VPD) sensor, a pupil dilation sensor, a body chemical sensor, a functional magnetic imaging (fMRI) sensor, a photoplethysmography (PPG) sensor, or a functional near-infrared data (fNIR) sensor. The sensor or sensors 328 may detect biometric data used as an indicator of the user's emotional state, for example, one or more of facial expression, skin temperature, pupil dilation, respiration rate, muscle tension, nervous system activity, pulse, EEG data, GSR data, fEMG data, EKG data, FAU data, BMI data, pupil dilation data, chemical detection (e.g., oxytocin) data, fMRI data, PPG data or fNIR data. In addition, the sensor(s) 328 may detect a user's context, for example an identity position, size, orientation and movement of the user's physical environment and of objects in the environment, motion or other state of a user interface display, for example, motion of a virtual-reality headset. Sensors may be built into wearable gear or non-wearable, including the display device itself, or in auxiliary equipment such as a smart phone, smart watch, or implanted medical monitoring device. Sensors may also be placed in nearby devices such as, for example, an Internet-connected microphone and/or camera array device used for hands-free network access.

Sensor data from the one or more sensors 328 may be processed locally by the CPU 302 to control display output, and/or transmitted to a server 200 for processing by the server in real time, or for non-real-time processing. As used herein, "real time" refers to processing responsive to user input without any arbitrary delay between inputs and outputs; that is, that reacts as soon as technically feasible. "Non-real time" or "offline" refers to batch processing or other use of sensor data that is not used to provide immediate control input for controlling the display, but that may control the display after some arbitrary amount of delay.

To enable communication with another node of a computer network, for example the directed content server 200, the client 300 may include a network interface 322, e.g., an Ethernet port, wired or wireless. Network communication may be used, for example, to enable multiplayer experiences, including immersive or non-immersive experiences of directed content. The system may also be used for non-directed multi-user applications, for example social networking, group entertainment experiences, instructional environments, video gaming, and so forth. Network communication can also be used for data transfer between the client and other nodes of the network, for purposes including data processing, content delivery, content control, and tracking. The client may manage communications with other network nodes using a communications module 306 that handles application-level communication needs and lower-level communications protocols, preferably without requiring user management.

A display 320 may be coupled to the processor 302, for example via a graphics processing unit 318 integrated in the processor 302 or in a separate chip. The display 320 may include, for example, a flat screen color liquid crystal (LCD) display illuminated by light-emitting diodes (LEDs) or other lamps, a projector driven by an LCD display or by a digital light processing (DLP) unit, a laser projector, or other digital display device. The display device 320 may be incorporated into a virtual reality headset or other immersive display system, or may be a computer monitor, home theater or television screen, or projector in a screening room or theater. Video output driven by a mixed reality display engine operating on the processor 302, or other application for coordinating user inputs with an immersive content display and/or generating the display, may be provided to the display device 320 and output as a video display to the user. Similarly, an amplifier/speaker or other audio output transducer 316 may be coupled to the processor 302 via an audio processor 312. Audio output correlated to the video output and generated by the media player module 308, directed content control engine or other application may be provided to the audio transducer 316 and output as audible sound to the user. The audio processor 312 may receive an analog audio signal from a microphone 314 and convert it to a digital signal for processing by the processor 302. The microphone can be used as a sensor for detection of emotional state and as a device for user input of verbal commands, or for social verbal responses to NPC's or other player actors.

The 3D environment apparatus 300 may further include a random-access memory (RAM) 304 holding program instructions and data for rapid execution or processing by the processor during controlling directed content in response to a user's emotional state. When the device 300 is powered off or in an inactive state, program instructions and data may be stored in a long-term memory, for example, a non-volatile magnetic, optical, or electronic memory storage device (not shown). Either or both RAM 304 or the storage device may comprise a non-transitory computer-readable medium holding program instructions, that when executed by the processor 302, cause the device 300 to perform a method or operations as described herein. Program instructions may be written in any suitable high-level language, for example, C, C++, C #, JavaScript, PHP, or Java™, and compiled to produce machine-language code for execution by the processor.

Program instructions may be grouped into functional modules 306, 308, to facilitate coding efficiency and comprehensibility. A communication module 306 may include coordinating communication of sensor data if metadata to a calculation server. A sensor control module 308 may include controlling sensor operation and processing raw sensor data for transmission to a calculation server. The modules 306, 308, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. The modules may be high-level modules only. The media player module 308 may perform operations of any method described herein, and equivalent methods, in whole or in part. Operations may be performed independently or in cooperation with another network node or nodes, for example, the server 200.

Figure 4:
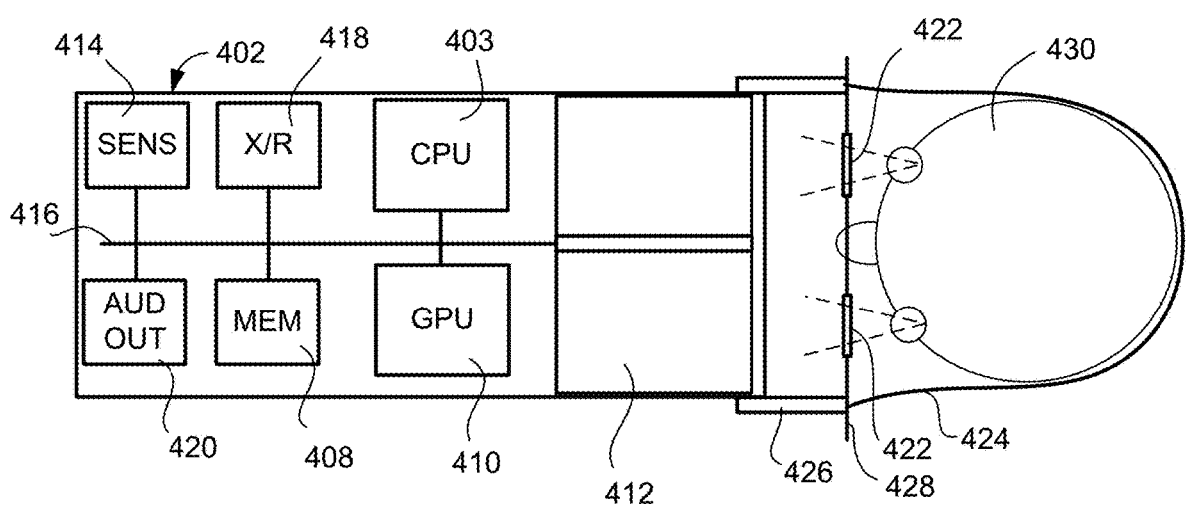
FIG. 4 is a schematic diagram showing features of a virtual-reality client device for digitally representing user engagement with audio-video content in a computer memory based on biometric sensor data.

In addition to conventional 2D output or 3D output for display on two-dimensional (flat or curved) screens (e.g., by televisions, mobile screens, or projectors), the content control methods disclosed herein may be used with Virtual Reality (VR) or Augmented Reality (AR) output devices. FIG. 4 is a schematic diagram illustrating one type of immersive VR stereoscopic display device 400, as an example of the client 300 in a more specific form factor. The client device 300 may be provided in various form factors, of which device 400 provides but one example. The innovative methods, apparatus and systems described herein are not limited to a single form factor and may be used in any video output device suitable for content output. As used herein, "directed content signal" includes any digital signal for audio-video output of directed content, which may be branching and interactive or non-interactive. In an aspect, the directed content may vary in response to a detected emotional state of the user.

The immersive VR stereoscopic display device 400 may include a tablet support structure made of an opaque lightweight structural material (e.g., a rigid polymer, aluminum or cardboard) configured for supporting and allowing for removable placement of a portable tablet computing or smartphone device including a high-resolution display screen, for example, an LCD display. The device 400 is designed to be worn close to the user's face, enabling a wide field of view using a small screen size such as in smartphone. The support structure 426 holds a pair of lenses 422 in relation to the display screen 412. The lenses may be configured to enable the user to comfortably focus on the display screen 412 which may be held approximately one to three inches from the user's eyes.

The device 400 may further include a viewing shroud (not shown) coupled to the support structure 426 and configured of a soft, flexible or other suitable opaque material for form fitting to the user's face and blocking outside light. The shroud may be configured to ensure that the only visible light source to the user is the display screen 412, enhancing the immersive effect of using the device 400. A screen divider may be used to separate the screen 412 into independently driven stereoscopic regions, each of which is visible only through a corresponding one of the lenses 422. Hence, the immersive VR stereoscopic display device 400 may be used to provide stereoscopic display output, providing a more realistic perception of 3D space for the user.

The immersive VR stereoscopic display device 400 may further comprise a bridge (not shown) for positioning over the user's nose, to facilitate accurate positioning of the lenses 422 with respect to the user's eyes. The device 400 may further comprise an elastic strap or band 424, or other headwear for fitting around the user's head and holding the device 400 to the user's head.

The immersive VR stereoscopic display device 400 may include additional electronic components of a display and communications unit 402 (e.g., a tablet computer or smartphone) in relation to a user's head 430. When wearing the support 426, the user views the display 412 though the pair of lenses 422. The display 412 may be driven by the Central Processing Unit (CPU) 403 and/or Graphics Processing Unit (GPU) 410 via an internal bus 417. Components of the display and communications unit 402 may further include, for example, a transmit/receive component or components 418, enabling wireless communication between the CPU and an external server via a wireless coupling. The transmit/receive component 418 may operate using any suitable high-bandwidth wireless technology or protocol, including, for example, cellular telephone technologies such as 3rd, 4th, or 5th Generation Partnership Project (3GPP) Long Term Evolution (LTE) also known as 3G, 4G, or 5G, Global System for Mobile communications (GSM) or Universal Mobile Telecommunications System (UMTS), and/or a wireless local area network (WLAN) technology for example using a protocol such as Institute of Electrical and Electronics Engineers (IEEE) 802.11. The transmit/receive component or components 418 may enable streaming of video data to the display and communications unit 402 from a local or remote video server, and uplink transmission of sensor and other data to the local or remote video server for control or audience response techniques as described herein.

Components of the display and communications unit 402 may further include, for example, one or more sensors 414 coupled to the CPU 403 via the communications bus 417. Such sensors may include, for example, an accelerometer/inclinometer array providing orientation data for indicating an orientation of the display and communications unit 402. As the display and communications unit 402 is fixed to the user's head 430, this data may also be calibrated to indicate an orientation of the head 430. The one or more sensors 414 may further include, for example, a Global Positioning System (GPS) sensor indicating a geographic position of the user. The one or more sensors 414 may further include, for example, a camera or image sensor positioned to detect an orientation of one or more of the user's eyes, or to capture video images of the user's physical environment (for VR mixed reality), or both. In some embodiments, a camera, image sensor, or other sensor configured to detect a user's eyes or eye movements may be mounted in the support structure 426 and coupled to the CPU 403 via the bus 416 and a serial bus port (not shown), for example, a Universal Serial Bus (USB) or other suitable communications port. The one or more sensors 414 may further include, for example, an interferometer positioned in the support structure 404 and configured to indicate a surface contour to the user's eyes. The one or more sensors 414 may further include, for example, a microphone, array or microphones, or other audio input transducer for detecting spoken user commands or verbal and non-verbal audible reactions to display output. The one or more sensors may include a subvocalization mask using electrodes as described by Arnav Kapur, Pattie Maes and Shreyas Kapur in a paper presented at the Association for Computing Machinery's ACM Intelligent User Interface conference in 2018. Subvocalized words might be used as command input, as indications of arousal or valance, or both. The one or more sensors may include, for example, electrodes or microphone to sense heart rate, a temperature sensor configured for sensing skin or body temperature of the user, an image sensor coupled to an analysis module to detect facial expression or pupil dilation, a microphone to detect verbal and nonverbal utterances, or other biometric sensors for collecting biofeedback data including nervous system responses capable of indicating emotion via algorithmic processing, including any sensor as already described in connection with FIG. 3 at 328.

Components of the display and communications unit 402 may further include, for example, an audio output transducer 420, for example a speaker or piezoelectric transducer in the display and communications unit 402 or audio output port for headphones or other audio output transducer mounted in headgear 424 or the like. The audio output device may provide surround sound, multichannel audio, so-called 'object oriented audio', or other audio track output accompanying a stereoscopic immersive VR video display content. Components of the display and communications unit 402 may further include, for example, a memory device 408 coupled to the CPU 403 via a memory bus. The memory 408 may store, for example, program instructions that when executed by the processor cause the apparatus 400 to perform operations as described herein. The memory 408 may also store data, for example, audio-video data in a library or buffered during streaming from a network node.

Having described examples of suitable clients, servers, and networks for performing methods of digitally representing user engagement with audio-video content in a computer memory based on biometric sensor data, more detailed aspects of these methods will be addressed. FIG. 5 illustrates an overview of a method 500 for calculation a Content Engagement Power (CEP), which may include four related operations in any functional order or in parallel. The operations may be programmed into executable instructions for a server as described herein.

A correlating operation 510 uses an algorithm to correlate biometric data for a user or user cohort to an emotional indicator. Optionally, the algorithm may be a machine-learning algorithm configured to process context-indicating data in addition to biometric data, which may improve accuracy. Context-indicating data may include, for example, user location, user position, time-of-day, day-of-week, ambient light level, ambient noise level, and so forth. For example, if the user's context is full of distractions, biofeedback data may have a different significance than in a quiet environment.

An emotional indicator may be a symbolic value that relates to an emotional arc. The indicator may have constituent elements, which may be quantitative or non-quantitative. For example, an indicator may be designed as a multi-dimensional vector with values representing intensity of psychological qualities such as cognitive load, arousal, and valence. Valence in psychology is the state of attractiveness or desirability of an event, object or situation; valence is said to be positive when a subject feels something is good or attractive and negative when the subject feels the object is repellant or bad. Arousal is the state of alertness and attentiveness of the subject. A machine learning algorithm may include at least one supervised machine learning (SML) algorithm, for example, one or more of a linear regression algorithm, a neural network algorithm, a support vector algorithm, a naïve Bayes algorithm, a linear classification module or a random forest algorithm.

An event detection operation 520 analyzes a time-correlated signal from one or more sensors during output of directed content to a user and detects events wherein the signal exceeds a threshold. The threshold may be a fixed predetermined value, or a variable number such as a rolling average. An example for GSR data is provided herein below. Discrete measures of emotional response may be calculated for each event. Emotions may not be measurable directly therefore sensor data indicates sentic modulation. Sentic modulations are modulations of biometric waveforms attributed to emotional states or changes in emotional states. In an aspect, to obtain baseline correlations between sentic modulations and emotional states, player actors may be shown a known visual stimulus (e.g., from focus group testing or a personal calibration session) to elicit a certain type of emotion. While under the stimulus, the test module may capture the player actor's biometric data and compare stimulus biometric data to resting biometric data to identify sentic modulation in biometric data waveforms.

A normalization operation 530 performs an arithmetic or other numeric comparison between test data for known stimuli and the measured signal for the user and normalizes the measured value for the event. Normalization compensates for variation in individual responses and provides a more useful output. Once the input sensor events are detected and normalized, a calculation operation 540 determines a CEP value for a user or user cohort and records the values in a time-correlated record in a computer memory.

Machine learning, also called AI, can be an efficient tool for uncovering correlations between complex phenomena. As shown in FIG. 6, a system 600 responsive to sensor data 610 indicating a user's emotional state may use a machine learning training process 630 to detect correlations between audio-video and narrative stimuli 620 and biometric data 610. The training process 630 may receive stimuli data 620 that is time-correlated to the biometric data 610 from media player clients (e.g., clients 300, 402). The data may be associated with a specific user or cohort or may be generic. Both types of input data (associated with a user and generic) may be used together. Generic input data can be used to calibrate a baseline for emotional response, to classify a baseline emotional response to a scene or arrangement of cinematographic elements. If most users exhibit similar biometric tells when viewing a scene within a narrative context, the scene can be classified with other scenes that provoke similar biometric data from users. The similar scenes may be collected and reviewed by a human creative producer, who may score the scenes on emotional indicator metrics 640 manually, assisted by automated analysis tools. In an alternative, the indicator data 640 can be scored by human and semi-automatic processing without being classed with similar scenes. These human-scored elements become training data for the machine learning process 630. In some embodiments, humans scoring elements of the directed content may include the users, such as via online survey forms. Scoring should consider cultural demographics and may be informed by expert information about responses of different cultures to scene elements.

The ML training process 630 compares human and machine-determined scores of scenes or other cinematographic elements and uses iterative machine learning methods as known in the art to reduce error between the training data and its own estimates. Creative content analysts may score data from multiple users based on their professional judgment and experience. Individual users may score their own content. For example, users willing to assist in training their personal "director software" to recognize their emotional states might score their own emotions while watching content. A problem with this approach is that the user scoring may interfere with their normal reactions, misleading the machine learning algorithm. Other training approaches include clinical testing of subject biometric responses over short content segments, followed by surveying the clinical subjects regarding their emotional states. A combination of these and other approaches may be used to develop training data for the machine learning process 630.

As used herein, biometric data provides a "tell" on how a user feels about their experience of directed content, i.e., are they engaged in the sense of entertainment value in narrative theory. Content Engagement Power is a measure of overall engagement throughout the user experience of directed content, monitored and scored during and upon completion of the experience. Overall user enjoyment is measured as the difference between expectation biometric data modulation power (as measured during calibration) and the average sustained biometric data modulation power. Measures of user engagement may be made by other methods and correlated to Content Engagement Power or made a part of scoring Content Engagement Power. For example, exit interview responses or acceptance of offers to purchase, subscribe, or follow may in included in or used to tune calculation of Content Engagement Power. Offer-response rates may be used during or after presentation of content to provide a more complete measure of user engagement.

The user's mood going into the interaction affects how the "story" is interpreted so the story experience should try to calibrate it out if possible. If a process is unable to calibrate out mood, then it may take it into account in the emotional arcs presented to favor more positively valenced interactions provided we can measure valence from the player actor. The instant system and methods will work best for healthy and calm individuals though it'll present an interactive experience for everyone who partakes.

Figure 7A:
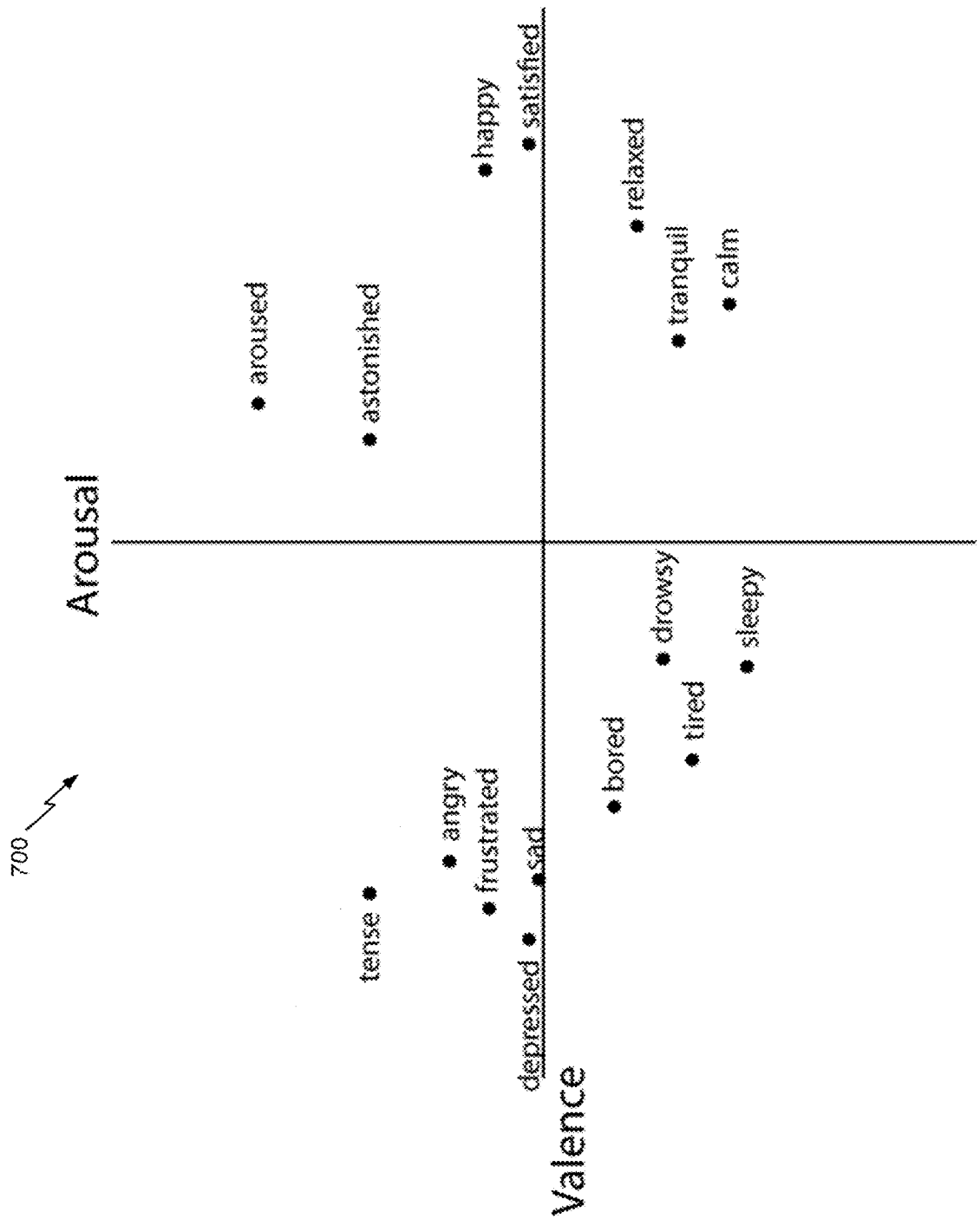
FIG. 7A is a diagram indicating an arrangement of emotional states relative to axes of a two-dimensional emotional space.

FIG. 7A shows an arrangement 700 of emotional states relative to axes of a two-dimensional emotional space defined by a horizontal valence axis and a vertical axis arousal. The illustrated emotions based on a valence/arousal emotional model are shown in the arrangement merely as an example, not actual or typical measured values. A media player client may measure valence with biometric sensors that measure facial action units, while arousal measurements may be done via GSR measurements for example.

Emotional spaces may be characterized by more than two axes. FIG. 7B diagrams a three-dimensional model 750 of an emotional space, wherein the third axis is social dominance or confidence. The model 750 illustrates a VAD (valence, arousal, confidence) model. The 3D model 1550 may be useful for complex emotions where a social hierarchy is involved. In another embodiment, an engagement measure from biometric data may be modeled as a three-dimensional vector which provides cognitive workload, arousal and valence from which a processor can determine primary and secondary emotions after calibration. Engagement measures may be generalized to an N-dimensional model space wherein N is one or greater. Presently, we base CEP in a two-dimensional space 700 with valence and arousal axes, but CEP is not limited thereby. For example, confidence is another psychological axis of measurement that might be added. Baseline arousal and valence may be determined on an individual basis during emotion calibration.

Emotion determination from biometric sensors is based on the valance/arousal emotional model where valance is (positive/negative) and arousal is magnitude. From this model we can verify the intention of the creative work by measuring narrative theory constructs such as tension (hope vs. fear) and rising tension (increase in arousal over time) and more change story elements dynamically based on the psychology of the user, as described in more detail in U.S. provisional patent application 62/614,811 filed Jan. 8, 2018. The present disclosure focuses on determining a useful measure of valance and arousal—the CEP—for real-time and offline applications, as described in more detail below.

In a test environment, electrodes and other sensors can be placed manually on subject users in a clinical function. For consumer application, sensor placement should be less intrusive and more convenient. For example, image sensors in visible and infrared wavelengths can be built into display equipment. Where a user wears gear or grasps a controller as when using VR equipment, electrodes can be built into headgear, controllers, and other wearable gear to measure skin conductivity, pulse, and electrical activity.

Emotional valence can be indicated and measured using facial displacement/voice spectral analysis. Facial analysis using facial action units as developed by Paul Ekman is one useful approach. For example, an application plugin developed by Affective provides a probability of a subject's emotion based on statistics and self-reported emotions against facial expressions. The plug-in works by producing probabilities of emotional valance based on spectral analysis (for voice) and mainly zygomaticus/corrugator movement for the face. To date Affective has measured over 7 million faces. It may be desirable to develop a methodology based on FAU optimized for evaluation of users consuming directed content. FIG. 8 shows a table 800 containing sample output from an instance of Affective evaluating FAUs from different users. Columns contain numeric measures of selected FAUs. Output may be optimized using machine learning or other techniques to identify the most telling FAUs for use in determining engagement measures for directed content.

Redundancy may be useful for reliability. A server may calculate valance and arousal multiple ways and use 2 for 1 voting to increase reliability and availability of valance and arousal measurements. For example, with redundant sensor inputs the server may weight galvanic skin response at 1, heart rate variability at 0.25, and % of maximum valance signal at 0.25. For further example, for valance sensor inputs the server may weight electroencephalography data at 1, and facial action unit data at 0.75. Several other measures of valence and arousal may also be useful, as summarized in the Table 1100 shown in FIG. 11. Indications of preferred inputs are based on practical considerations and may change as the techniques are refined. Highly-weighted input is believed to be more accurate or reliable than lower-weighted input. All data sources will rarely be available, even in test environments. Nonetheless, numerous measurement options are available to system designers, as summarized below.

Electroencephalography (EEG) pre-frontal asymmetry analysis may be a useful method to measure approach versus avoidance as an emotional tell for valance. Sensors measure voltage potentials of neurons passing through the brain and calculate alpha wave power for the different hemispheres. Power variation across the two hemispheres is a tell for approach and avoidance or positive versus negative emotion. For example, a frontal asymmetry index may be calculated as the log of a ratio of right hemisphere power to left hemisphere power, and correlates to approach vs. avoidance or positive vs. negative valence.

It may also be possible to measure arousal using the strength of a valence measurement. For example, a measurement system may be used to measure the MAX muscle displacement of the face during a smile. Arousal is then surmised by a ratio of current to MAX displacement or other comparative calculation.

Figure 9:
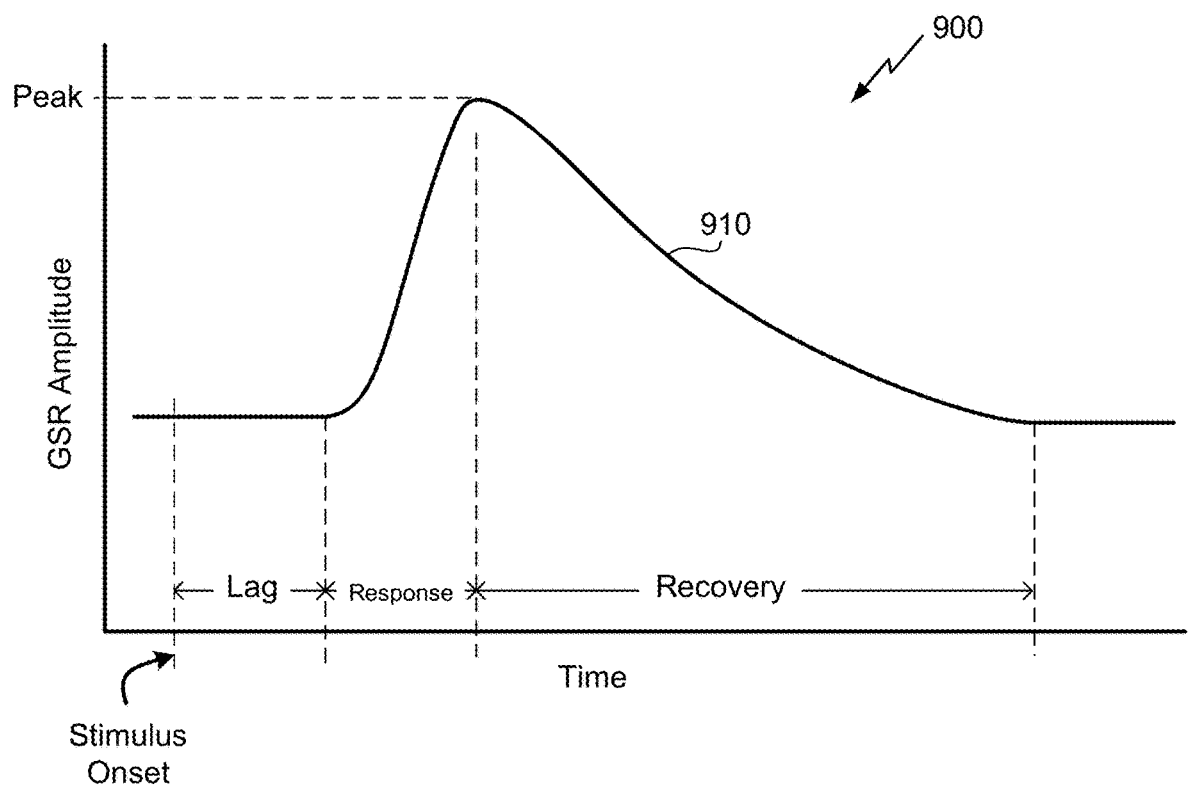
FIG. 9 is a chart illustrating a peak Galvanic Skin Response (GSR) useful for correlating to emotional arousal.

Emotional arousal may be measured by a variety of methods, including Galvanic Skin Impulse (phasic) response. When a subject is aroused a rapid change in skin resistance occurs that can be measured by sending a small current through the body and measuring resistance. FIG. 9 illustrates a GSR peak response over time. The number of impulse responses (peaks) observed over time correlate to the strength of the arousal. Thus, the simplest measure of event power is $E_P=C$, wherein '$E_P$' is event power and 'C' is the number of times the signal exceeds the applicable threshold. Additionally, the peak amplitude is also a tell of the strength of the arousal which may be converted into arousal power. For example, the expression $\Sigma P_a$ wherein '$P_a$' is the peak amplitude of each event provides a measure of event power for the content. An equivalent unitless measure of event power is given by $\Sigma P_a/S_{avg}$, wherein '$S_{avg}$' is an average signal value for the content. Both measurement methods may be useful. Another useful measure may be the integrated area under the amplitude curve. For example, the area between the signal response line 1010 and a fixed threshold 1020 or a variable threshold 1030 may be calculated where the signal is above the threshold line. Event count, peak amplitudes and integrated areas may be combined in any useful manner. For example, the expression $(CP_a t+A)/S_{avg} t$ wherein 'A' is the total area defined by the signal line when above the threshold line, is a minimum time increment (e.g., 1 second), and the other symbols are as defined above provides a unitless measure of event power for any segment of content. Other measures may also be of interest, for example, event power per unit of time. Event power per unit time may be derived by dividing any of the foregoing unitless event powers by the running length of the content.

Figure 10:
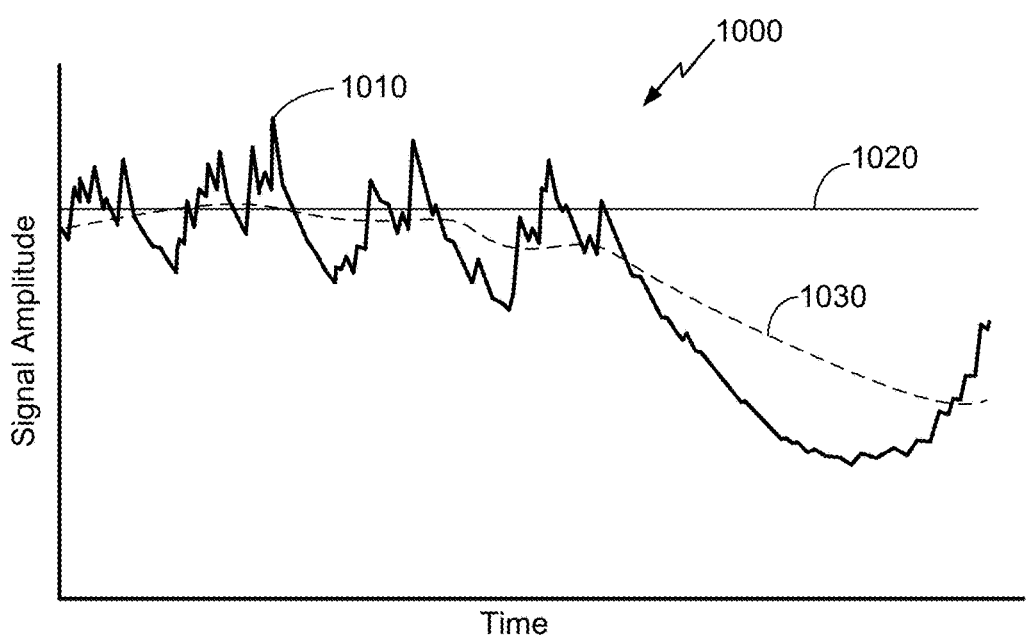
FIG. 10 is chart illustrating combined tonic and phasic GSR response over time for correlating to emotional arousal.

Galvanic Skin Tonic response is a slower resistance response that is also indicative of arousal. Major DC shifts in the signal are a signifier for arousal. A graph 1000 of combined tonic and phasic GSR responses 1010 is shown in FIG. 10. A fixed threshold value 1020 may be used to detect events used in calculating CEP. In an alternative, a variable threshold value 1030, for example a rolling average, may be used to compensate for longer-term variability.

A server may calculate arousal power consumption from peak amplitude using $P(DC)=I^2R$ where current is equal to supplied current from the GSR circuit. It may also calculate arousal DC power shifts using the same equation but for the tonic response. The two can be combined for an overall impulse (phasic) power response and a tonic power response for arousal, based on GSR.

While FIG. 10 indicates arousal amplitude for GSR or any other quantitative signal indicating arousal, similar measures may be used to calculate event power for any desired valance measurement. Different measurements may be needed for different valance qualities.

Facial action units have already been discussed in connection with FIG. 8. Output of an FAU analysis can be processed using a rule-based algorithm and/or machine learning to detect valance and arousal. FAU should have high reliability and wide measurement range for normally expressive users. It may also be of use in detecting arousal, although reliability is currently unproven.

Heart rate variability (HRV) is another useful measure of emotional valence, shown in the table of FIG. 11 as pulse detection (line 4). Pulse may be detected using electrodes, audio or vibration analysis, listening or feeling for the pulse using an audio sensor or accelerometer. Pulse can also be detected by image analysis. Blood pressure variation during the heartbeat pulse causes visible effects in the face or extremities that may be detected using an image sensor and image processor. A healthy individual has a heart rate variation frequency greater than 0.15 hertz. Lower frequency HRV following a stimulus is attributed to sympathetic nervous system responses related to arousal. During an experience the server determining CEP may monitor HRV during calibration and throughout the user's experience as an arousal tell. Similarly, heart rate increase is a measure of emotional valence. The CEP server may monitor the user's heart rate during calibration and throughout the user's experience as an arousal tell. It may calculate a percentage change in heart rate and apply thresholds to detect arousal events. For example, if heart rate is greater than 10% of baseline and if heart rate variability is greater than 0.15 Hz then the subject is aroused.

Pupil dilation (line 5) is a reliable indication of arousal and can be detected using image analysis. Functional near infrared (fNIR, line 6) is relatively easy to implement using an infrared sensor calibrated to work in the range of human skin temperature. Skin temperature indicates both arousal and valance when used to confirm other measurements.

Facial Electromyography (fEMG) is EMG applied to muscles of the face. It has been known to be useful for emotion detection. Contraction and relaxation of muscle fibers generates an electrical signal that can be detected by electrode pairs attached across specific muscle groups. Two muscle groups in the face may be particularly useful, the corrugator supercilii group used for frowning and the zygomaticus major muscle group used for smiling. However, frowning, smiling and other expressions may be detected without need for the user to wear electrodes, using images analysis and facial action units. In mixed reality (VR or AR) applications where the users wear headgear that blocks imaging of facial expression, fEMG may provide an alternative for gathering data correlating to emotional response.

Subvocalization may be considered a species of fEMG that can detect activity of muscle groups associated with speech. The user wears a partial mask that holds an electrode array against selected areas of the jaw, neck, and chin just outside of the lower lip. A neural network can be trained to detect the user's subvocalization to an accuracy greater than 90%. Subvocalized speech can be used for any purpose speech is used for. In calculation of engagement power, spontaneous subvocalized speech (e.g., exclamations) can indicate both arousal and valance. Unlike facial expression, subvocalization is not detectable using image analysis. Hence, the use of a facial mask for subvocalization may be most desirable where users wish to speak to a game or other entertainment process without making a sound.

Electrocardiography (EKG) measures contraction and relaxation of the heart muscle using electrodes attached to the chest and/or back of the subject. It is used in health care for patient monitoring and diagnosis of cardiac disease. EKG provides a more detailed picture of cardiac activity that may provide more information regarding arousal than a simple pulse. In an alternative, a simplified form of EKG may be used where it is more convenient than other methods of pulse detection. For example, where a user is wearing an EKG module (e.g., in a smartwatch, fitness tracker, or other gear) with one or more electrodes positioned for pulse sensing, a data gathering module may receive a signal from the EKG module and process the signal for pulse detection or another characteristic of the cardiac signal, such as heart rate variability (HRV).

Brain Machine Interface (BMI) refers to implanted electrodes or other electrical or electro-chemical sensors responsive to brain activity. BMI devices may be of use in clinical settings but are not likely to be in use by consumers for the foreseeable future. BMI is mentioned here as a future possibility if the technology becomes available in consumer applications.

Functional Magnetic Resonance Imaging (fMRI) measures brain activity by detecting blood flow. Unlike conventional MRI, fMRI detects changes in tissue over time by detecting blood oxygen level. Hence fMRI correlates well to brain activity and is useful for sensing activity or inactivity in different brain areas. However, fMRI equipment is bulky and not practical for use outside of clinical settings, at present.

Chemical detection equipment varies in complexity and bulk, from spectroscopy to micro or nanosensors specialized for specific chemicals. Micro or nano sensors incorporated into output gear are likely to be most practical initially. For example, a chemical sensor incorporating one or more microelectronic chemical sensors may be placed in headgear near the nose and mouth. In an alternative or in addition, sensors may be placed on the skin to detect chemicals excreted in sweat. Chemicals and compounds of interest for detecting arousal and valance may include, for example, cortisol, adrenaline, norepinephrine, oxytocin, acetylcholine, dopamine, endorphins, seratonin and pheromones. However, many of these chemicals may be difficult to detect using external sensors.

Gaze direction (line 13) is easy to detect using image analysis. Depth of focus may also be detected by measuring corneal flexing. Direction and depth of focus do not indicate valance or arousal but do indicate interest. User interest may be useful for control of content or for better utilizing other sensor data. For example, if a user is looking at the "wrong" content while their data indicates an error in valance or arousal, the error may be weighted less for momentary distraction.

Target emotional arcs based on directed content can stored in a computer database as valance/arousal targets. A server may perform a difference calculation to determine the error between the planned/predicted and measured emotional arousal and valance. The error may be used in content control. Once a delta between the predict and measured passes a threshold then a correction will be commanded by the story management software. If the user's valance is in the wrong direction as governed by the predict (based on target emotional arc) then the processor may change the content by the following logic: If absolute value of (Valance Predict−Valance Measured)>0 then Change Content. The change in content can be several different items specific to what the software has learned about the player-actor or it can be a trial or recommendation from an AI process. Likewise, if the arousal error falls below 50% of predicted (Absolute value of (error)>0.50*Predict) then the processor may change the content. The change in content can be several different items specific to what the software has learned about the player-actor or it can be a trial or recommendation from an AI process.

Figure 12:
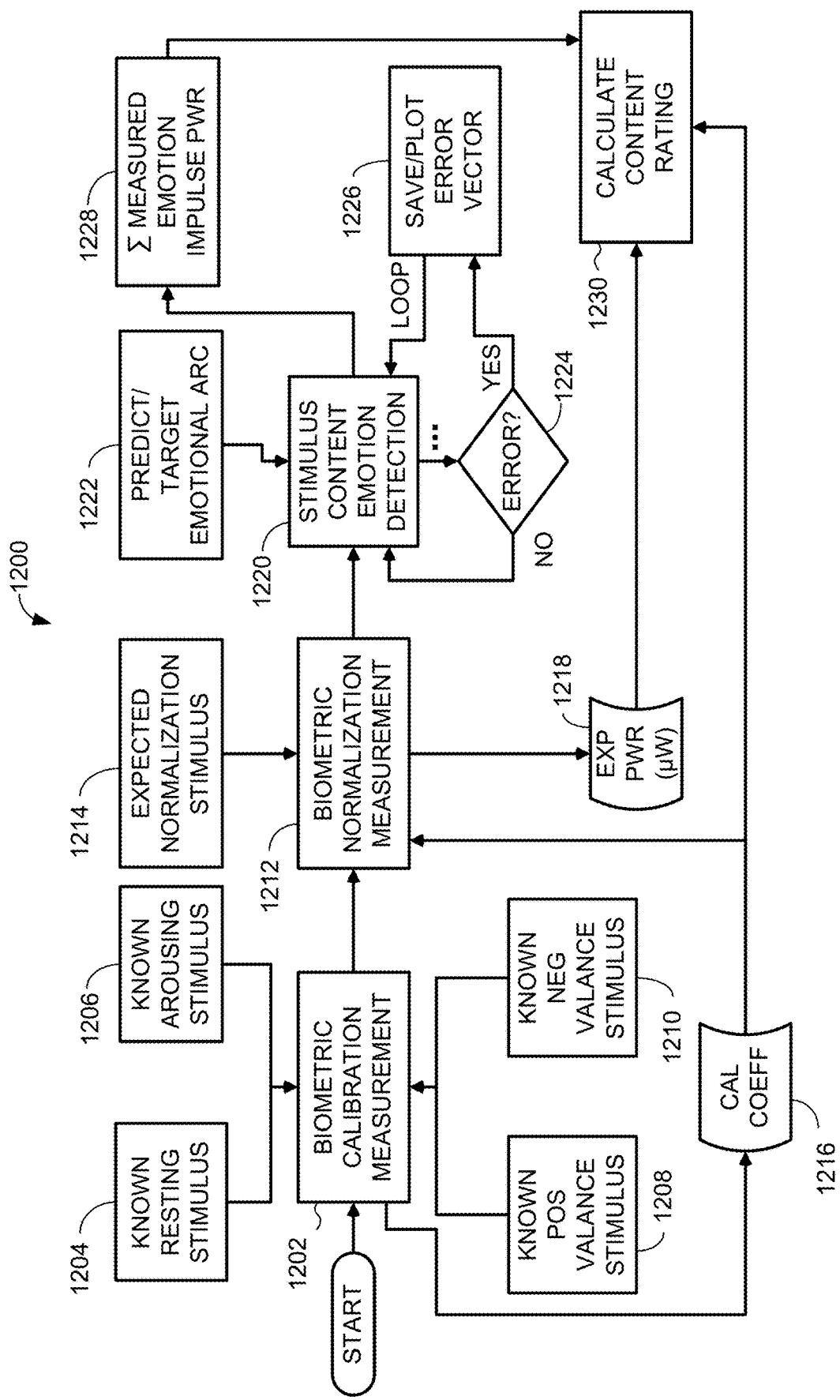
FIG. 12 is a flow chart illustrating a process for determining a content rating based on biometric response data.

FIG. 12 shows a method 1200 for determining a content rating for audio-video content, including Content Engagement Power (CEP). CEP is a ratio of a sum of event power '$P_v$' for the subject content to expectation power '$P_x$' for comparable content in the genre. $P_v$ and $P_x$ are calculated using the same methodology for different subject matter and in the general case for different users. As such, the sums cover different total times, event power $P_v$ covering a time period '$t_v$' that equals a sum of 'n' number of event power periods $\Delta t_v$ for the subject content:

$$t_v = \sum_n^1 \Delta t_v \qquad \text{Eq. 1}$$

Likewise, expectation power $P_x$ covers a period '$t_x$' that equals a sum of 'm' number of event power periods $\Delta t_x$ for the expectation content:

$$t_x = \sum_m^1 \Delta t_x \qquad \text{Eq. 2}$$

Each of powers $P_v$ and $P_x$ is, for any given event 'n' or 'm', a dot product of a power vector P and a weighting vector W of dimension i, as follows:

$$P_{v_n} = \vec{P_v} \cdot \vec{W} = \sum_i^1 P_{v_i} W_i = P_{v_1} W_1 + P_{v_2} W_2 + \ldots + P_{v_i} W_i \qquad \text{Eq. 3}$$

$$P_{x_m} = \vec{P_x} \cdot \vec{W} = \sum_i^1 P_{x_i} W_i = P_{x_1} W_1 + P_{x_2} W_2 + \ldots + P_{x_i} W_i \qquad \text{Eq. 4}$$

In general, the power vector $\vec{P}$ can be defined variously. In any given computation of CEP the power vectors for the subject content and the expectation baseline should be defined consistently with one another, and the weighting vectors should be identical. A power vector may include arousal measures only, valance values only, a combination of arousal measures and valance measures, or a combination of any of the foregoing with other measures, for example a confidence measure. In one embodiment, CEP is calculated using power vectors $\vec{P}$ defined by a combination of 'j' arousal measures '$a_j$' and 'k' valance measures '$v_k$', each of which is adjusted by a calibration offset 'C' from a known stimulus, wherein j and k are any non-negative integer, as follows:

$$\vec{P}_c = (a_1 C_1, \ldots, a_j C_j, v_1 C_{j+1}, \ldots, v_k C_{j+k}) \qquad \text{Eq. 5}$$

wherein $$C_j = S_j - S_j O_j = S_j (1 - O_j) \qquad \text{Eq. 6}$$

The index 'j' in Equation 6 signifies an index from 1 to j+k, $S_j$ signifies a scaling factor and $O_j$ signifies the offset between the minimum of the sensor data range and its true minimum. A weighting vector W corresponding to the power vector of Equation 5 may be expressed as:

$$\vec{W} = (w_1, \ldots, w_j, w_{j+1}, \ldots, w_k) \qquad \text{Eq. 7}$$

wherein each weight value scales its corresponding factor in proportion to the factor's relative estimated reliability.

With calibrated dot products $p_{v_n}$, $P_{x_m}$ given by Equations 3 and 4 and time factors as given by Equations 1 and 2, a processor may compute a content engagement power (CEP) for a single user as follows:

$$CEP_{user}(dBm) = 10 \cdot \log_{10}\left(\frac{\sum_n^1 P_v \Delta t_v}{\sum_m^1 P_x \Delta t_x} \cdot \frac{t_x}{t_v}\right) \qquad \text{Eq. 8}$$

The ratio $t_x/t_v$ normalizes inequality in the disparate time series sums and renders the ratio unitless. A user CEP value greater than 1 indicates that a user/player actor/viewer has had an emotionally engaging experience above their expectations relative to the genre. A user CEP value less than 1 indicates that engagement is less than the user's expectations for the content genre.

CEP can also be calculated for content titles across audiences of 'v' users as a ratio of the content event power for the 'x' users to the expectation power for 'm' not necessarily identical users, as follows:

$$CEP_{title}(dBm) = 10 \cdot \log_{10}\left(\frac{\sum_{v}^{1}\sum_{n}^{1}P_{v}\Delta t}{\sum_{x}^{1}\sum_{m}^{1}P_{x}\Delta t} \cdot \frac{xt_x}{vt_v}\right) \qquad \text{Eq. 9}$$

The variables v and x are the number of content users and engagement baseline viewers, respectively. The audience expectation power in the denominator represents the expectation that the audience brings to the content, while event power in the numerator represents the sum of the audience's arousal or valance events while experiencing the content. The processor sums the event power over each event (n) and user (v), and the expectation power over each event (m) and user (x). It then calculates the CEP by calculating the ratio of event power to expectation power, and normalizing disparate time sums and audience counts by the ratio $xt_x/vt_v$. The CEP is a component of content rating. Other components of content rating may include aggregate valance error and valance error for particular valance targets (e.g., triumph, despair, etc.)

Equation 5 describes a calibrated power vector made up of arousal and valance measures derived from biometric sensor data. In an alternative, the processor may define a partially uncalibrated power vector in which the sensor data signal is scaled as part of lower-level digital signal processing before conversion to a digital value but not offset for a user as follows:

$$\vec{P} = (a_1, \ldots, a_j, v_1, \ldots, v_k) \qquad \text{Eq.10}$$

If using a partially uncalibrated power vector, an aggregate calibration offset may be computed for each factor and subtracted from the dot products $P_{v_n}$, $P_{x_m}$ given by Equations 3 and 4 before calculating Content Engagement Power (CEP). For example, an aggregate calibration offset for $P_{v_n}$ may be given by:

$$C_v = i(\vec{C_v} \cdot \vec{W}) = i\sum_{i}^{1}C_{v_i}W_i = C_{v_1}W_1 + C_{v_2}W_2 + \ldots + C_{v_i}W_i \qquad \text{Eq. 11}$$

In such case, a calibrated value of the power vector $P_{v_n}$ can be computed by:

$$P_{v_n} - C_{v_n} \qquad \text{Eq. 12}$$

The calibrated power vector can be similarly computed.

Referring again to the method 1200 in which the foregoing expressions can be used (FIG. 12), a calibration process 1202 for the sensor data is first performed to calibrate user reactions to known stimuli, for example a known resting stimulus 1204, a known arousing stimulus 1206, a known positive valance stimulus 1208, and a known negative valance stimulus 1210. The known stimuli 1206-1210 can be tested using a focus group that is culturally and demographically like the target audience and maintained in a database for use in calibration. For example, the International Affective Picture System (ZAPS) is a database of pictures for studying emotion and attention in psychological research. For consistency with the content platform, images or these found in the IAPS or similar knowledge bases may be produced in a format consistent with the targeted platform for use in calibration. For example, pictures of an emotionally-triggering subject can be produced as video clips. Calibration ensures that sensors are operating as expected and providing data consistently between users. Inconsistent results may indicate malfunctioning or misconfigured sensors that can be corrected or disregarded. The processor may determine one or more calibration coefficients 1216 for adjusting signal values for consistency across devices and/or users.

Calibration can have both scaling and offset characteristics. To be useful as an indicator of arousal, valance, or other psychological state, sensor data may need calibrating with both scaling and offset factors. For example, GSR may in theory vary between zero and 1, but in practice depend on fixed and variable conditions of human skin that vary across individuals and with time. In any given session, a subject's GSR may range between some $GSR_{min}>0$ and some $GSR_{max}<1$. Both the magnitude of the range and its scale may be measured by exposing the subject to known stimuli and estimating the magnitude and scale of the calibration factor by comparing the results from the session with known stimuli to the expected range for a sensor of the same type. In many cases, the reliability of calibration may be doubtful, or calibration data may be unavailable, making it necessary to estimate calibration factors from live data. In some embodiments, sensor data might be pre-calibrated using an adaptive machine learning algorithm that adjusts calibration factors for each data stream as more data is received and spares higher-level processing from the task of adjusting for calibration.

Once sensors are calibrated, the system normalizes the sensor data response data for genre differences at 1212, for example using Equation 8 or 9. Different genres produce different valance and arousal scores. For example, action-adventure genres have a different pace, emotional target, and intensity. Thus, engagement power cannot be compared across genres unless the engagement profile of the genre is considered. Genre normalization scores the content relative to content in the same genre, enabling comparison on an equivalent basis across genres. Normalization 1212 may be performed on a test audience or focus group, or on the subject group prior to the main feature, using an expected normalization stimulus 1214. For example, the audience may view one or more trailers in the same genre as the main feature, and event power may be calculated for the one or more trailers. In an alternative, archived data for the same users or same user cohort may be used to calculate expectation power. Expectation power is calculated using the same algorithms as used or will be used for measurements of event power and can be adjusted using the same calibration coefficients 1216. The processor stores the expectation power 1218 for later use.

At 1220, a processor receives sensor data during play of the subject content and calculates event power for each measure of concern, such as arousal and one or more valance qualities. At 1228, the processor sums or otherwise aggregates the event power for the content after play is concluded, or on a running basis during play. At 1230, the processor calculates the content rating, including the content engagement power (CEP) as previously described. The processor first applies applicable calibration coefficients and then calculates the CEP by dividing the aggregated event power by the expectation power as described above.

Optionally, the calculation function 1220 may include comparing, at 1224, an event power for each detected event, or for a lesser subset of detected events, to a reference emotional arc defined for the content. A reference arc may be, for example, a targeted arc defined by a creative producer, a predicted arc, a past arc or arcs for the content, or a combination of the foregoing. At 1226, the processor may save, increment or otherwise accumulate an error vector value describing the error for one or more variables. The error vector may include a difference between the references arc and a measured response for each measured value (e.g., arousal and valance values) for a specified scene, time period, or set of video frames. The error vector and matrix of vectors may be useful for content evaluation or content control.

Error measurements may include or augment other metrics for content evaluation. Content engagement power and error measurements may be compared to purchases, subscriptions, or other conversions related to presented content. The system may also measure consistency in audience response, using standard deviation or other statistical measures. The system may measure content engagement power, valance and arousal for individual, cohorts, and aggregate audiences.

Figure 13:
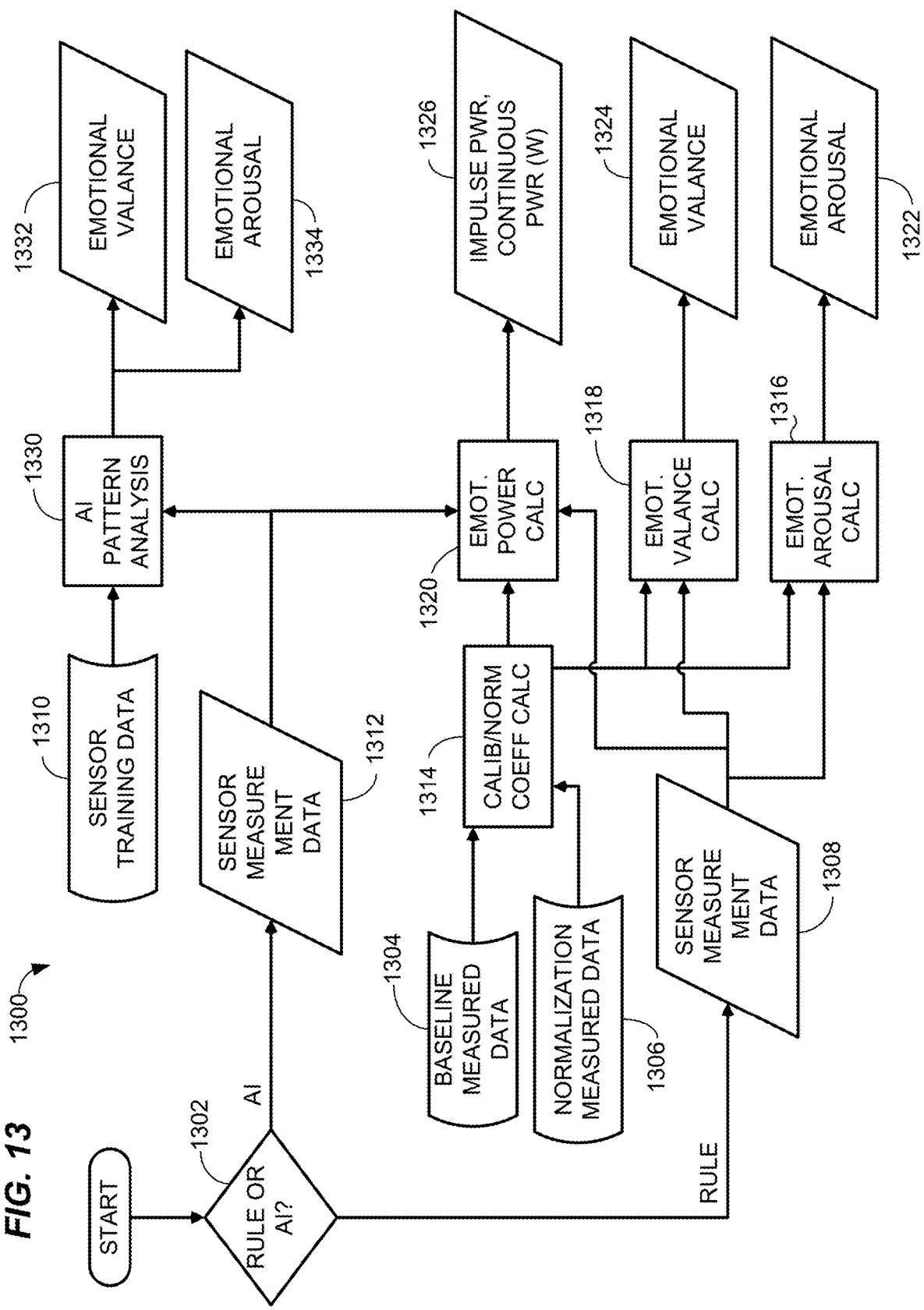
FIG. 13 is a flow chart illustrating a process for determining valance, arousal and content engagement power measurements.

Referring to FIG. 13, alternative methods 1300 for measuring emotional valance and arousal and determining content engagement power 1326 diverge at 302 into an AI-based branch and a rule-based branches. However, other suitable methods may combine AI and rule-based approaches in various ways. Both branches start with sensor data 1312, 1308. Separate flows objects 1312, 1308 are shown for illustrative simplicity but both branches may use the same sensor data, which originate from any one or more of the biometric sensors described herein.

On the AI branch, the sensor measurement data 1312 along with the sensor training data 1310 are inputs to a machine learning pattern analysis process 1330 that outputs measurements of emotional valance, arousal and event power values for an emotional power calculation process 1320 as described herein. The power calculation 1320 may omit calibration and normalization when using AI-derived data, because calibration and normalization are handled as an integral part of the machine learning process. In a sense, normalization and calibration are embedded in the training data 1310. Examples of suitable AI processes are described herein in connection with FIG. 6. Output from the AI process branch should correlate to rule-based output but will not be the same because of the use of different algorithms. The power calculation process 1320 compares different measures of arousal, event power and expectation power and derives from them content engagement power, as described above. Although derived from arousal measurements, content engagement power 1336 is a unitless, comparative measure for entire content titles or major subcomponents, based on power impulses or continuous measures. CEP 1336 differs from arousal data 1334 that is not comparative and is correlated to specific times or frames in video content, for error determination or content profiling.

On the rule-based branch, baseline sensor data 1304 for calibration and expectation sensor data 1306 are accessed by a rule-based process 1314 for determining calibration and normalization coefficients as previously described. The calibration and normalization coefficients are output to downstream rule-based calculation processes, including the emotional power calculation process 1320 and emotional power calculation process 1320, the valance calculation process 1318 and the arousal calculation process 1316. Sensor measurement data is likewise input to the three calculation processes. Valance output 1324 and arousal output 1322 are time-correlated valance and arousal amplitude from one or more sensor inputs. Measurements from different sensor types may be combined and weighted according to reliability as summarized herein above.

Figure 14:
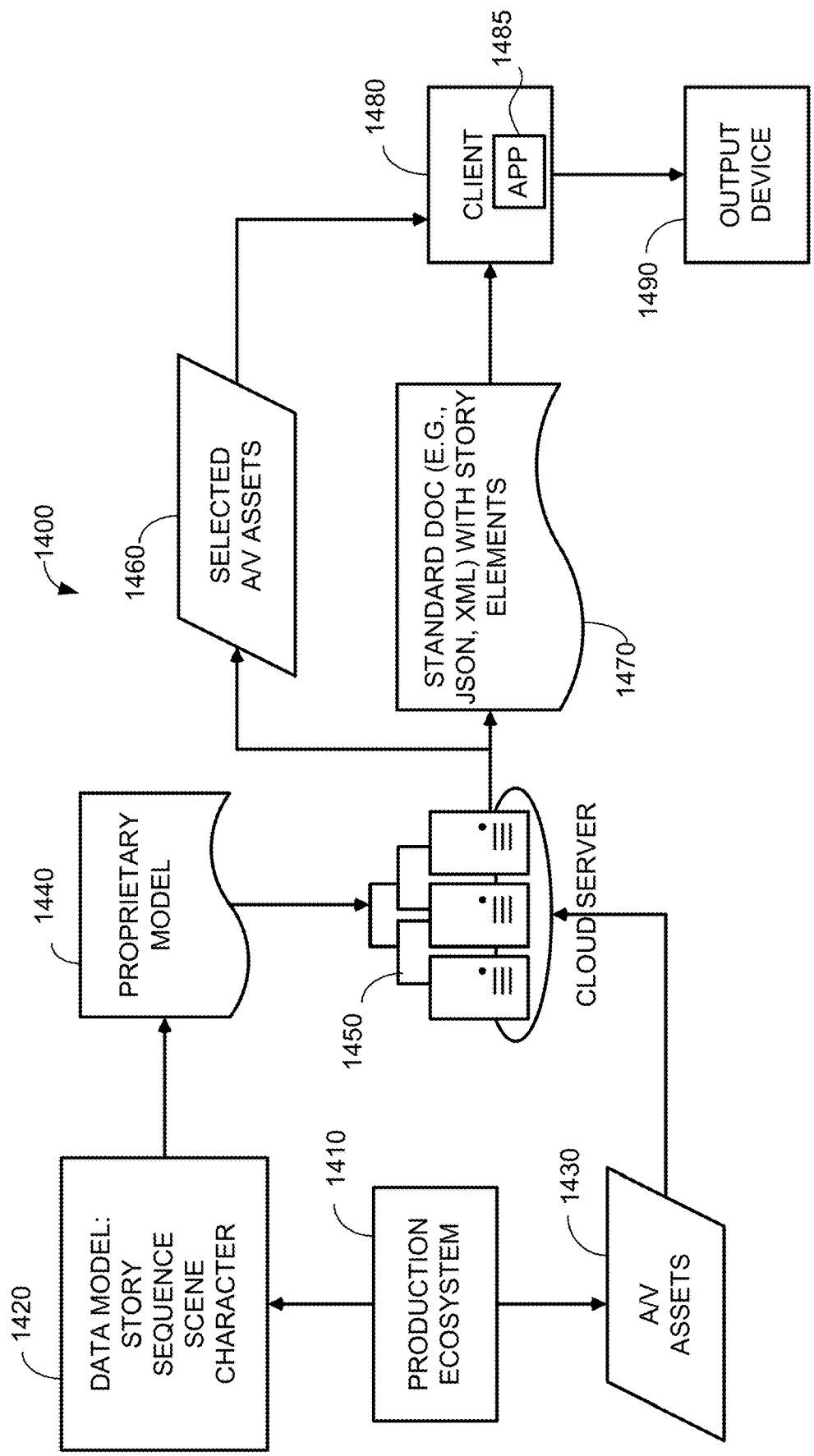
FIG. 14 is a block diagram illustrating a data handling use case for content responsive to biometric valance and arousal data.

FIG. 14 shows a system 1400 for producing and distributing configurable content responsive to valance and arousal data. A production ecosystem 1410 produces a data model 1420 for content and related digital audio-video assets 1430. Besides video and audio clips, the AN data 1430 may include 3D modeling and rendering data, video and digital objects for virtual reality or augmented reality, metadata, and any other digital asset needed during playout. The data model 1420 defines content elements such as story, sequence, scene, dialog, emotional arc, and character. Elements can be fixed or configurable. For example, a configurable story may be defined as a branching narrative. In an alternative, the narrative may be fixed, and configurable elements limited to supporting features such as character or object appearances and alternative phrases for expressing lines of dialog. The data model 1420 may be expressed in a proprietary formal 1440 and provided to a data server 1450 with the audio-video assets 1430 needed for play-out. The cloud server 1450 may also be provided with an application that generates a control document 1470 for the story elements in a standard format, for example JavaScript Object Notation (JSON) or Extensible Markup Language (XML), suitable for use on the destination platform. The control document 1470 may include a definition of a targeted emotional arc for the content.

The cloud server 1450 provides the story element control document 1470 with audio-video content 1460 selected for the destination user and platform. For example, assets 1460 provided for mobile platforms may differ from assets for home theater, both of which differ from assets for cinema or virtual reality experiences. For further example, content for an adult user may differ from content designated for a young child. Many other reasons for different content selection may apply. The story element control document 1460 may be tailored for the selected content and may configured for use by a JavaScript or similar content viewing application executing on the client 1480. The viewing application 1485 on the client 1480 may be configured to receive sensor input, for example as described above in connection with FIGS. 3-4. Based on the sensor input and story element document 1470, the application 1485 may execute a process for reducing valance and/or arousal error detected by comparing sensor input to expected values of the emotional arc. The application may use a trial-and-error approach augmented with available information about past user responses and preferences to choose alternative story elements. The selected elements are provided to the output device 1490, which produces audible output using an audio transducer and a visible display using a screen, projector, or other opto-electric device. Other outputs may include, for example, motion, tactile, or olfactory outputs. The system 1400 illustrates a use case for real-time content control by a client device. Real-time control may also be implemented at a server level for content streamed to the client.

Figure 15:
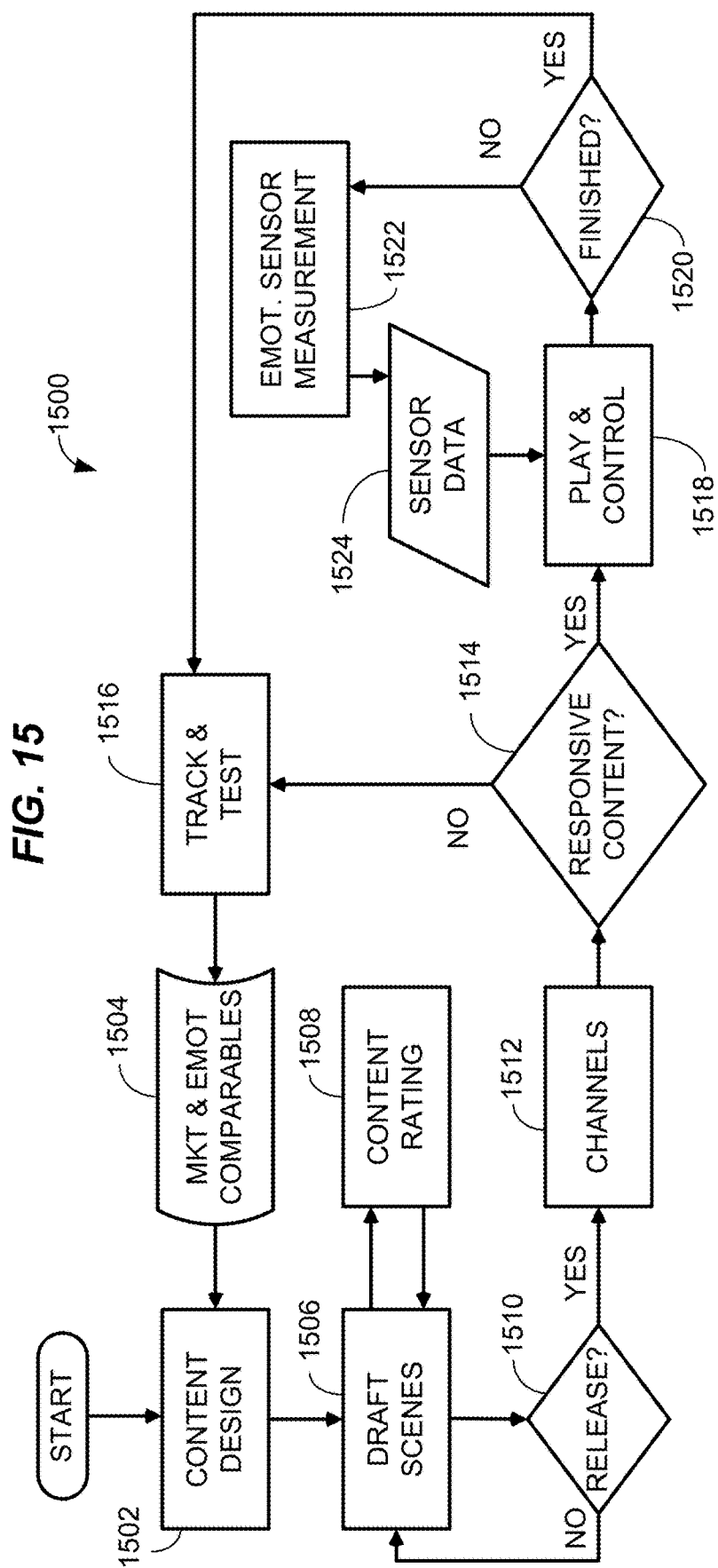
FIG. 15 is a flow chart illustrating use cases for digital representations of user engagement in production and distribution of content.

FIG. 15 illustrates a method 1500 for showing a method 1500 that includes both an offline use case and a real-time control case for sensor-based content ratings including content engagement power and specific valance and arousal time or content correlated matrices. The method 1500 begins with content design 1502, which receives as one of its inputs marketing and emotional response (e.g., content rating) data for past comparable products. Input may also include a target emotional arc. In an alternative, the emotional arc may be defined during content design 1502. Once content design 1502 defines desired scenes and scene sequences, preparation of draft scenes may begin at 1506. Drafts may be completed for testability with a focus group that experiences the draft output and generates biometric emotional response sensor data that can processed and rated to prepare a content rating 1508, as described herein above. The production team reviews the content ratings and revises the draft scene. Once revisions are complete, the content rating process 1508 may be applied again to draft version of the content title. Once the title is ready for release at 1510, it enters one or more distribution channels. If the content is not responsive to emotional feedback data, market analytic teams may use the tools and techniques described herein to test and track 1516 emotional response as another marketing metric. Emotional response data can be added to the marketing and content ratings data 1504 for use in design of future products. Referring back to 1514, if the content is responsive it is provided for playout and control 1518. During playout, media players receive and process emotional response sensor data 1524 from measuring 1522 by one or more biometric emotional sensors as described herein. Once each playout device completes play, it can process sensor feedback to develop content ratings or submit the feedback data to a server (not shown). Once the content ratings for the content are completed, they may be added to the content ratings data 1504 for use in future product design.

In view the foregoing, and by way of additional example, FIGS. 16-18 show aspects of a method 1600 or methods for digitally representing user engagement with audio-video content in a computer memory based on biometric sensor data, and related functions. The method 1600 may be performed by an immersive mixed reality output device or a non-immersive flat screen device, projector, or other output device including a programmable computer, by one or more computers in communication with the output device, or by a combination of an output device and one or more computers in communication with the output device.

Referring to FIG. 16, a computer-implemented method for digitally representing user engagement with audio-video content in a computer memory based on biometric sensor data may include, at 1610, playing digital data comprising audio-video content by an output device that outputs audio-video output based on the digital data. The output device may be, or may include, a portable or non-portable flat screen device, a digital projector, or wearable gear for alternative reality or augmented reality, in each case coupled to an audio output capability and optionally to other output capabilities (e.g., motion, tactile, or olfactory). Playing the digital data may include, for example, keeping the digital data in a cache or other memory of the output device and processing the data for output by at least one processor of the output device.

The method 1600 may include, at 1620, receiving by the at least one computer processor sensor data from at least one sensor positioned to sense an involuntary response of one or more users while engaged with the audio-video output. The sensor data may include any one or more of the data described herein, for example, the measurement type data summarized in FIG. 11.

The method 1600 may include, at 1630, determining by an algorithm executing by the at least one computer processor at least one digital representation of Content Engagement Power (CEP) based on the sensor data. The algorithm may include, for example, calculating a ratio of aggregate event power to aggregate expectation power for comparable content in the genre. Aggregate event power may be a sum of sensor amplitudes indicative of arousal for events defined by exceeding a threshold. Aggregate expectation power may be calculated for the comparable content by the same method as event power. Further details and illustrative examples of the algorithm may be as described herein above in connection with FIG. 11. The method 1600 may include, at 1640, recording the at least one digital representation of CEP in a computer memory.

The method 1600 may include any one or more of additional operations 1700 or 1800, shown in FIGS. 17-18, in any operable order. Each of these additional operations is not necessarily performed in every embodiment of the method, and the presence of any one of the operations 1700 or 1800 does not necessarily require that any other of these additional operations also be performed.

Referring to FIG. 17 showing certain additional operations or aspects 1700 for digitally representing user engagement with audio-video content in a computer memory based on biometric sensor data, the method 1600 may further include, at 1710, determining the at least one digital representation of CEP at least in part by determining arousal values based on the sensor data and comparing a stimulation average arousal based on the sensor data with an expectation average arousal. For sensing arousal, the sensor data may include any one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, body chemical sensing data, functional magnetic imaging (fMRI) data, and functional near-infrared data (fNIR).

In a related aspect, the method 1600 may include, at 1720, determining the expectation average arousal based on further sensor data measuring a like involuntary response of the one or more users while engaged with known audio-video stimuli, for example, comparable content in the same genre as the content. Comparable content may include same-genre content intended for a similar audience and platform, and of similar length. In a related aspect, the method 1600 may include, at 1730, playing the known audio-video stimuli comprising a known non-arousing stimulus and a known arousing stimulus, for calibration of sensor data. At 1740, determining the at least one digital representation of CEP of the method 1600 may further include detecting one or more stimulus events based on the sensor data exceeding a threshold value for a time period. In such cases, the method 1600 may include calculating one of multiple event powers for each of the one or more users and for each of the stimulus events and aggregating the event powers. In an aspect, the processor may assign weights to each of the event powers based on one or more source identities for the sensor data. Additional explanation of these operations and event power is described above in connection with FIG. 10.

In a related aspect, the method 1600 may include, at 1750, determining the expectation average arousal at least in part detecting one or more stimulus events based on the further sensor data exceeding a threshold value for a time period, and calculating one of multiple expectation powers for the known audio-video stimuli for the one or more users and for each of the stimulus events. In addition, at 1760, determining the at least one digital representation of CEP may include calculating a ratio of the sum of the event powers to an aggregate of the expectation powers, as shown in the expression provided herein above in connection with FIG. 12.

Referring to FIG. 18 showing certain additional operations 1800, the method 1600 may further include, at 1810, determining an arousal error measurement based on comparing the arousal values to a targeted emotional arc for the audio-video content. The targeted emotional arc may be, or may include, a set of targeted digital representations of valence each uniquely associated with a different interval of a continuous time sequence or frame sequence for digital audio-video content. Error may be measured by a difference of values, a ratio of values, or a combination of a difference and a ratio, for example, (Target−Actual)/Target. In a related aspect, the method 1600 may further include, at 1820, determining digital representations of valence based on the sensor data. The digital representation of valance may include a quantitative measure indicative of an amplitude or power of the sensor signal(s) that corresponds to magnitude of a detected emotion. Suitable sensor data for valance may include, for example, one or more of electroencephalographic (EEG) data, facial electromyography (fEMG) data, video facial action unit (FAU) data, brain machine interface (BMI) data, functional magnetic imaging (fMRI) data, body chemical sensing data, subvocalization data and functional near-infrared data (fNIR). The method 1600 may include, for example, determining a digital representation of valence based on the sensor data, for example by a computer processor filtering to remove noise and distortion, normalizing to a scale, and transforming to a time-correlated list of symbolic numeric values expressed in binary code.

In a related aspect, the method 1600 may further include, at 1830, normalizing the digital representations of valence based on like values collected for the known audio-video stimuli. "Like values" means values collected using the same methods and processing algorithms as the digital representations of valance, or values transformed to be comparable using those same representations. The known stimuli may include calibration stimuli and normalization stimuli as described herein above. The normalizing operation 1830 makes use of normalization stimuli from similar content in the same genre as the content for which valance error is calculated.

In another related aspect, the method 1600 may further include, at 1840, determining a valence error measurement based on comparing the digital representations of valence to a targeted emotional arc for the audio-video content. The targeted emotional arc may include a set of targeted digital representations of valence each uniquely associated with a different interval of a continuous time sequence or frame sequence. A frame sequence is a form of time sequence for content running at a constant frame rate.

In another aspect, the at least one digital representation of CEP comprises a sequence of digital representations of CEP wherein each member of the sequence is calculated based on a discrete period in the audio-video content. The discrete period may be defined by a time or by frame count. The method 1600 may further include, at 1850, outputting a symbolic representation of the at least one digital representation of CEP to at least one of a display screen or an audio transducer.

Emotional feedback can also be used for controlling or influencing live entertainment. Accordingly, the method 1600 may include, at 1850, recording the digital data comprising audio-video content of a live performance by at least one actor and outputting the representation of CEP and/or of valance or arousal error, or equivalent measures to the display screen or audio transducer arranged to be perceivable by the at least one actor during the live performance. For example, the display screen may include a stage monitor and the audio transduce may be incorporated into an earpiece. Hence, the actor can receive detailed information about valance and arousal and adjust the performance to reach targeted goals.

Figure 19:
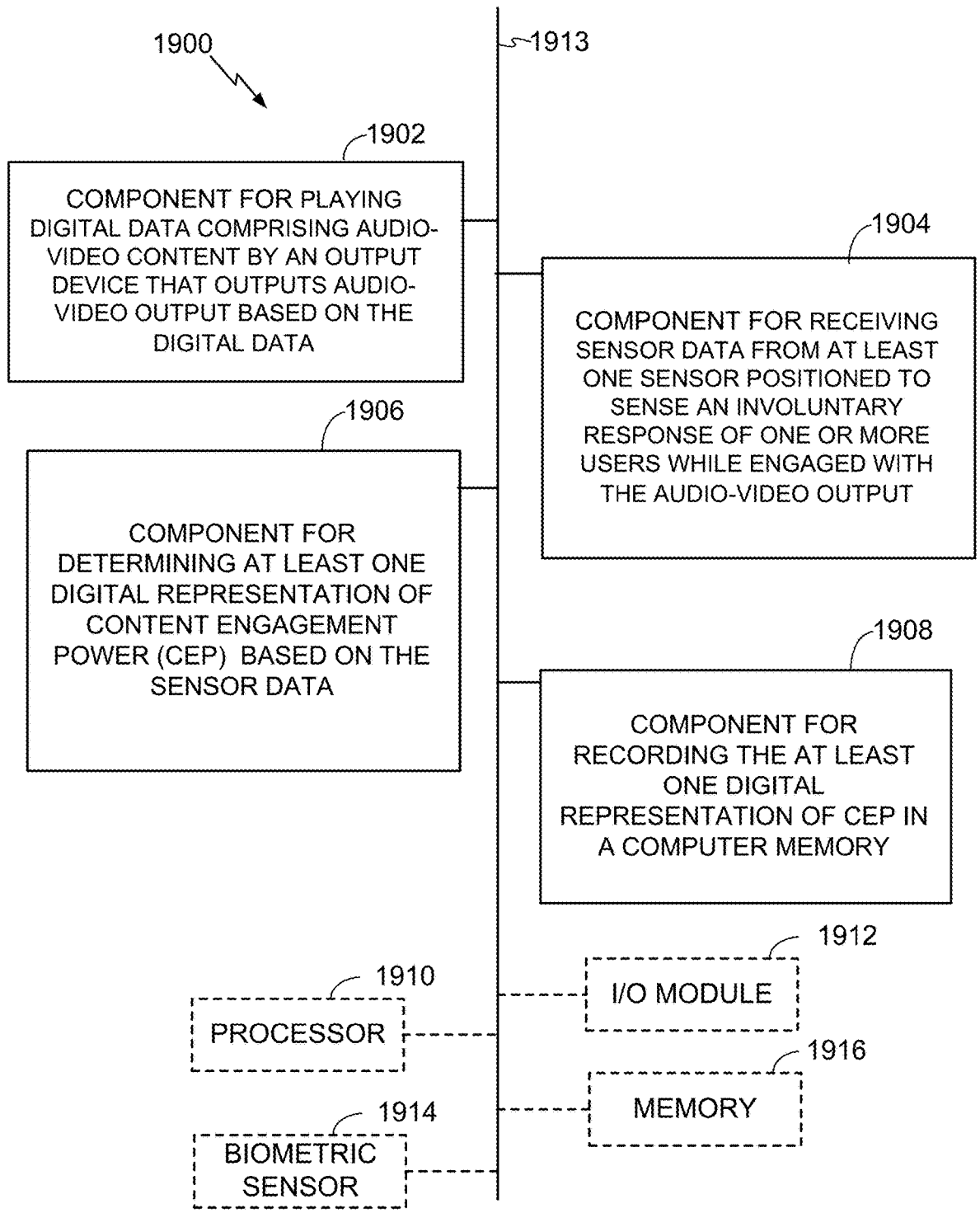
FIG. 19 is a conceptual block diagram illustrating components of an apparatus or system for digitally representing user engagement with audio-video content in a computer memory based on biometric sensor data.

FIG. 19 is a conceptual block diagram illustrating components of an apparatus or system 1900 for digitally representing user engagement with audio-video content in a computer memory, and related functions. The apparatus or system 1900 may include additional or more detailed components for performing functions or process operations as described herein. For example, the processor 1910 and memory 1916 may contain an instantiation of a process for representing user engagement with audio-video content in a computer memory as described herein above. As depicted, the apparatus or system 1900 may include functional blocks that can represent functions implemented by a processor, software, or combination thereof (e.g., firmware).

As illustrated in FIG. 19, the apparatus or system 1900 may comprise an electrical component 1902 for playing digital data comprising audio-video content by an output device that outputs audio-video output based on the digital data. The component 1902 may be, or may include, a means for said playing. Said means may include the processor 1910 coupled to the memory 1916, and to an output of a at least one biometric sensor 1914, the processor executing an algorithm based on program instructions stored in the memory. Such algorithm may include, for example, reading metadata describing the audio-video content, opening one or more files stored on a computer readable medium or receiving the audio-video data via a streaming connection, decoding the audio-video content and producing a digital video stream and a digital audio stream from the content, and directing the streams to respective video and audio processors.

The apparatus 1900 may further include an electrical component 1904 for receiving sensor data from at least one sensor positioned to sense an involuntary response of one or more users while engaged with the audio-video output. The component 1904 may be, or may include, a means for said receiving. Said means may include the processor 1910 coupled to the memory 1916, the processor executing an algorithm based on program instructions stored in the memory. Such algorithm may include a sequence of more detailed operations in parallel to the player component 1902, for example, checking one or more port assigned for receiving sensor data, decoding data received at the assigned port, checking data quality and optionally executing an error routine if data quality fails testing, and saving the decoded sensor data in a cache memory location defined for use by the components 1904 and 1906.

The apparatus 1900 may further include an electrical component 1906 for determining at least one Content Engagement Power (CEP) value, based on the sensor data. The component 1906 may be, or may include, a means for said determining. Said means may include the processor 1910 coupled to the memory 1916, the processor executing an algorithm based on program instructions stored in the memory. Such algorithm may include a sequence of more detailed operations, for example, as described in connection with FIG. 12.

The apparatus 1900 may further include an electrical component 1908 for recording the at least one digital representation of CEP in a computer memory. The component 1908 may be, or may include, a means for said recording. Said means may include the processor 1910 coupled to the memory 1916, the processor executing an algorithm based on program instructions stored in the memory. Such algorithm may include a sequence of more detailed operations, for example, connecting to an application that maintains a database or other data structure for storing the CEP and other content ratings, encoding the CEP in a message with relevant relational data such as content title and time period or frame set per the application's program interface (API), and sending the message according to the API.

The apparatus 1900 may optionally include a processor module 1910 having at least one processor. The processor 1910 may be in operative communication with the modules 1902-1908 via a bus 1913 or similar communication coupling. In the alternative, one or more of the modules may be instantiated as functional modules in a memory of the processor. The processor 1910 may initiate and schedule the processes or functions performed by electrical components 1902-1908.

In related aspects, the apparatus 1900 may include a network interface module 1912 or equivalent I/O port operable for communicating with system components over a computer network. A network interface module may be, or may include, for example, an Ethernet port or serial port (e.g., a Universal Serial Bus (USB) port), a WiFi interface, or a cellular telephone interface. In further related aspects, the apparatus 1900 may optionally include a module for storing information, such as, for example, a memory device 1916. The computer readable medium or the memory module 1916 may be operatively coupled to the other components of the apparatus 1900 via the bus 1913 or the like. The memory module 1916 may be adapted to store computer readable instructions and data for effecting the processes and behavior of the modules 1902-1908, and subcomponents thereof, or the processor 1910, the method 1600 and one or more of the additional operations 1700-1800 disclosed herein, or any method for performance by a media player described herein. The memory module 1916 may retain instructions for executing functions associated with the modules 1902-1908. While shown as being external to the memory 1916, it is to be understood that the modules 1902-1908 can exist within the memory 1916 or an on-chip memory of the processor 1910.

The apparatus 1900 may include, or may be connected to, one or more biometric sensors 1914, which may be of any suitable types. Various examples of suitable biometric sensors are described herein above. In alternative embodiments, the processor 1910 may include networked microprocessors from devices operating over a computer network. In addition, the apparatus 1900 may connect to an output device as described herein, via the I/O module 1912 or other output port.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the application and design constraints imposed on the overall system. Skilled artisans may implement the described functionality in varying ways for each application, but such implementation decisions should not be interpreted as causing a departure from the scope of the present disclosure.

As used in this application, the terms "component", "module", "system", and the like are intended to refer to a computer-related entity, either hardware, a combination of hardware and software, software, or software in execution. For example, a component or a module may be, but are not limited to being, a process running on a processor, a processor, an object, an executable, a thread of execution, a program, and/or a computer. By way of illustration, both an application running on a server and the server can be a component or a module. One or more components or modules may reside within a process and/or thread of execution and a component or module may be localized on one computer and/or distributed between two or more computers.

Various aspects will be presented in terms of systems that may include several components, modules, and the like. It is to be understood and appreciated that the various systems may include additional components, modules, etc. and/or may not include all the components, modules, etc. discussed in connection with the figures. A combination of these approaches may also be used. The various aspects disclosed herein can be performed on electrical devices including devices that utilize touch screen display technologies, heads-up user interfaces, wearable interfaces, and/or mouse-and-keyboard type interfaces. Examples of such devices include VR output devices (e.g., VR headsets), AR output devices (e.g., AR headsets), computers (desktop and mobile), televisions, digital projectors, smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device (PLD) or complex PLD (CPLD), discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, digital versatile disk (DVD), Blu-Ray™, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a client device or server. In the alternative, the processor and the storage medium may reside as discrete components in a client device or server.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips, or other format), optical disks (e.g., compact disk (CD), DVD, Blu-Ray™ or other format), smart cards, and flash memory devices (e.g., card, stick, or other format). Of course, those skilled in the art will recognize many modifications may be made to this configuration without departing from the scope of the disclosed aspects.

The previous description of the disclosed aspects is provided to enable any person skilled in the art to make or use the present disclosure. Various modifications to these aspects will be clear to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

In view of the exemplary systems described supra, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers.

The invention claimed is:

1. A computer-implemented method for digitally representing user engagement with audio-video content in a computer memory, the method comprising:
    playing digital data comprising audio-video content by an output device that outputs audio-video output based on the digital data;
    receiving by at least one computer processor sensor data from at least one sensor positioned to sense an involuntary response of one or more users while engaged with the audio-video output;
    determining by an algorithm executing by the at least one computer processor at least one digital representation of Content Engagement Power (CEP) based on the sensor data, comprising determining arousal values based on the sensor data and comparing a stimulation average arousal based on the sensor data with an expectation average arousal;
    determining an arousal error measurement based on comparing the arousal values to a targeted emotional arc for the audio-video content; and
    recording the at least one digital representation of CEP in a computer memory.

2. The method of claim 1, wherein the sensor data comprises one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, body chemical sensing data, functional magnetic imaging (fMRI) data, and functional near-infrared data (fNIR).

3. The method of claim 1, further comprising determining the expectation average arousal based on further sensor data measuring a like involuntary response of the one or more users while engaged with known audio-video stimuli.

4. The method of claim 3, further comprising playing the known audio-video stimuli comprising a known non-arousing stimulus and a known arousing stimulus.

5. The method of claim 3, wherein determining the at least one digital representation of CEP further comprises detecting one or more stimulus events based on the sensor data exceeding a threshold value for a time period.

6. The method of claim 5, further comprising calculating one of multiple event powers for each of the one or more users and for each of the stimulus events, and aggregating the event powers.

7. The method of claim 6, further comprising assigning weights to each of the event powers based on one or more source identities for the sensor data.

8. The method of claim 6, wherein determining the expectation average arousal further comprises detecting one or more stimulus events based on the further sensor data exceeding a threshold value for a time period, and calculating one of multiple expectation powers for the known audio-video stimuli for the one or more users and for each of the stimulus events.

9. The method of claim 8, wherein determining the at least one digital representation of CEP comprises calculating a ratio of the sum of the event powers to an aggregate of the expectation powers.

10. The method of claim 1, wherein the targeted emotional arc comprises a set of targeted arousal values each uniquely associated with a different interval of a continuous time sequence.

11. The method of claim 1 wherein the at least one digital representation of CEP comprises a sequence of digital representations of CEP wherein each member of the sequence is calculated based on a discrete period in the audio-video content.

12. The method of claim 1, further comprising outputting a symbolic representation of the at least one digital representation of CEP to at least one of a display screen or an audio transducer.

13. The method of claim 12, further comprising recording the digital data of a live performance by at least one actor and outputting the digital representation to the display screen or the audio transducer arranged to be perceivable by the at least one actor.

14. An apparatus for digitally representing user engagement with audio-video content in a computer memory, comprising a processor coupled to a memory, the memory holding program instructions that when executed by the processor cause the apparatus to perform:
    playing digital data comprising audio-video content by an output device that outputs audio-video output based on the digital data;
    receiving sensor data from at least one sensor positioned to sense an involuntary response of one or more users while engaged with the audio-video output;
    determining at least one Content Engagement Power (CEP) value, based on the sensor data, at least in part by determining arousal values based on the sensor data and comparing a stimulation average arousal based on the sensor data with an expectation average arousal;
    determining an arousal error measurement based on comparing the arousal values to a targeted emotional arc for the audio-video content; and
    recording the at least one digital representation of CEP in a computer memory.

15. A computer-implemented method for digitally representing user engagement with audio-video content in a computer memory, the method comprising:
    playing digital data comprising audio-video content by an output device that outputs audio-video output based on the digital data;

receiving by at least one computer processor sensor data from at least one sensor positioned to sense an involuntary response of one or more users while engaged with the audio-video output;

determining by an algorithm executing by the at least one computer processor at least one digital representation of Content Engagement Power (CEP) based on the sensor data, comprising determining arousal values based on the sensor data and comparing a stimulation average arousal based on the sensor data with an expectation average arousal;

determining a digital representation of valence based on the sensor data;

measuring an involuntary response of the one or more users while engaged with known audio-video stimuli;

normalizing the digital representations of valence based on values collected for the known audio-video stimuli; and recording the at least one digital representation of CEP in a computer memory.

16. The method of claim 15, wherein the sensor data comprises one or more of electroencephalographic (EEG) data, facial electromyography (fEMG) data, video facial action unit (FAU) data, brain machine interface (BMI) data, functional magnetic imaging (fMRI) data, body chemical sensing data, subvocalization data and functional near-infrared data (fNIR).

17. The method of claim 15, further comprising determining a valence error measurement based on comparing the digital representations of valence to a targeted emotional arc for the audio-video content.

18. The method of claim 17, wherein the targeted emotional arc comprises a set of targeted digital representations of valence each uniquely associated with a different interval of a continuous time sequence.

* * * * *